(12) United States Patent
Nishimi et al.

(10) Patent No.: US 8,585,972 B2
(45) Date of Patent: Nov. 19, 2013

(54) BIOSENSOR

(75) Inventors: Taisei Nishimi, Kanagawa (JP);
Toshihide Ezoe, Kanagawa (JP);
Toshiaki Kubo, Kanagawa (JP);
Hidetoshi Tomita, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 612 days.

(21) Appl. No.: 12/778,555

(22) Filed: May 12, 2010

(65) Prior Publication Data

US 2010/0221845 A1 Sep. 2, 2010

Related U.S. Application Data

(62) Division of application No. 11/358,107, filed on Feb. 22, 2006.

(30) Foreign Application Priority Data

| Feb. 23, 2005 | (JP) | 2005-046977 |
| Jun. 3, 2005 | (JP) | 2005-163454 |
| Jun. 3, 2005 | (JP) | 2005-163455 |
| Jun. 3, 2005 | (JP) | 2005-163456 |

(51) Int. Cl.
*G01N 33/53* (2006.01)

(52) U.S. Cl.
USPC ............ 422/82.01; 514/100; 435/23; 435/29; 435/7.1; 435/7.92; 435/6.1

(58) Field of Classification Search
None
See application file for complete search history.

(56) References Cited

U.S. PATENT DOCUMENTS

| 5,032,282 | A | 7/1991 | Linder et al. |
| 5,242,828 | A | 9/1993 | Bergstrom et al. |
| 5,543,054 | A | 8/1996 | Charkoudian et al. |
| 6,322,979 | B1 | 11/2001 | Bamdad et al. |
| 2001/0008765 | A1 | 7/2001 | Shinoki et al. |
| 2002/0110933 | A1 | 8/2002 | Wagner et al. |
| 2002/0128234 | A1* | 9/2002 | Hubbell et al. ............... 514/100 |
| 2003/0032046 | A1 | 2/2003 | Duffy et al. |
| 2003/0153014 | A1* | 8/2003 | Shen et al. ..................... 435/7.9 |

FOREIGN PATENT DOCUMENTS

| EP | 1293779 A2 | 3/2003 |
| JP | 2003-028872 A | 1/2003 |
| JP | 2004-317295 A | 11/2004 |
| JP | 2005-017155 A | 1/2005 |
| JP | 2005-030883 A | 2/2005 |
| JP | 2005-062074 A | 3/2005 |

(Continued)

OTHER PUBLICATIONS

Office Action dated Oct. 12, 2010 on corresponding JP Application No. 2005-163454.

(Continued)

*Primary Examiner* — N. C. Yang
(74) *Attorney, Agent, or Firm* — Sughrue Mion, PLLC

(57) ABSTRACT

One object of the present invention is to provide a biosensor and a production method therefor, by which hydrogel that enables immobilization of a physiologically active substance can be conveniently produced using safe raw materials. The present invention provides a biosensor which comprises a substrate having a metal layer on its surface, wherein a hydrophilic polymer having a reactive functional group capable of reacting with a hydroxyl group or an amino group of a physiologically active substance is bound to the metal layer directly or indirectly via an intermediate layer.

15 Claims, 4 Drawing Sheets

(56) References Cited

FOREIGN PATENT DOCUMENTS

| JP | 2006-234472 A | 9/2006 |
|---|---|---|
| JP | 2006-266746 A | 10/2006 |
| WO | 98/47000 A2 | 10/1998 |
| WO | 02/057422 A2 | 7/2002 |
| WO | 03/075012 A1 | 9/2003 |
| WO | 2004/046724 A1 | 6/2004 |
| WO | 00/65352 A1 | 1/2008 |

OTHER PUBLICATIONS

Japanese Official Action dated, Dec. 8, 2009.

"Affi-Gel® 10 and 15 Activated Affinity Media", BIO-RAD Tech Note 1085.

Sahni et al,. "Binding of Basic Fibroblast Growth Factor to Fibrinogen and Fibrin". J. Biol. Chem. vol. 273, No. 13 pp. 7554-7559, 1998.

European Official Action dated Dec. 14, 2007.

Johnsson B et al, "Immobilization of Proteins to a Carboxymethyldextran-Modified Gold Surface for Biospecific Interaction Analysis in Surface Plasmon Resonance Sensors", Analytical Biochemistry, Academic Press, San Diego, CA, US, vol. 198, No. 2, Nov. 1, 1991, pp. 268-277.

Lofas S et al, "A Novel Hydrogel Matrix on Gold Surfaces in Surface Plasmon Resonance Sensors for Fast and Efficient Covalent Immobilization of Ligands", Journal of the Chemical Society, Chemical Communications, Chemical Society Letchworth, GB, No. 21, 1990, pp. 1526-1528.

Lofas S et al, "Methods for Site Controlled Coupling to Carboxymethyldextran Surfaces in Surface Plasmon Resonance Sensors", Biosensors & Bioelectronics, Elsevier Science Publishers, Barking, GB, vol. 10, No. 9, 1995, pp. 813-822.

\* cited by examiner

BIOSENSOR

This is a divisional of application Ser. No. 11/358,107 filed Feb. 22, 2006. The entire disclosure of the prior application, application Ser. No. 11/358,107, is hereby incorporated by reference.

TECHNICAL FIELD

The present invention relates to a biosensor and a method for analyzing an interaction between biomolecules using the biosensor. Particularly, the present invention relates to a biosensor which is used for a surface plasmon resonance biosensor and a method for analyzing an interaction between biomolecules using the biosensor. Further, the present invention relates to an agent for immobilizing a physiologically active substance, which comprises a polymer. More specifically, the present invention relates to an agent for immobilizing a physiologically active substance, which is used for chemically immobilizing a physiologically active substance such as a protein on an organic or inorganic substrate, a thin film, or a fine particle.

BACKGROUND ART

Recently, a large number of measurements using intermolecular interactions such as immune responses are being carried out in clinical tests, etc. However, since conventional methods require complicated operations or labeling substances, several techniques are used that are capable of detecting the change in the binding amount of a test substance with high sensitivity without using such labeling substances. Examples of such a technique may include a surface plasmon resonance (SPR) measurement technique, a quartz crystal microbalance (QCM) measurement technique, and a measurement technique of using functional surfaces ranging from gold colloid particles to ultra-fine particles. The SPR measurement technique is a method of measuring changes in the refractive index near an organic functional film attached to the metal film of a chip by measuring a peak shift in the wavelength of reflected light, or changes in amounts of reflected light in a certain wavelength, so as to detect adsorption and desorption occurring near the surface. The QCM measurement technique is a technique of detecting adsorbed or desorbed mass at the ng level, using a change in frequency of a crystal due to adsorption or desorption of a substance on gold electrodes of a quartz crystal (device). In addition, the ultra-fine particle surface (nm level) of gold is functionalized, and physiologically active substances are immobilized thereon. Thus, a reaction to recognize specificity among physiologically active substances is carried out, thereby detecting a substance associated with a living organism from sedimentation of gold fine particles or sequences.

In all of the above-described techniques, the surface where a physiologically active substance is immobilized is important. Surface plasmon resonance (SPR), which is most commonly used in this technical field, will be described below as an example.

A commonly used measurement chip comprises a transparent substrate (e.g., glass), an evaporated metal film, and a thin film having thereon a functional group capable of immobilizing a physiologically active substance. The measurement chip immobilizes the physiologically active substance on the metal surface via the functional group. A specific binding reaction between the physiological active substance and a test substance is measured, so as to analyze an interaction between biomolecules.

As an example of a detection surface having a functional group by which a physiologically active substance can be immobilized, JP Patent No. 2815120 discloses in detail a method for producing hydrogel. Specifically, a barrier layer is formed by the binding of 16-mercaptohexadecanol layer to a gold film. On the gold film, the hydroxyl group of the barrier layer is epoxy-activated by treatment with epichlorohydrin. At the next stage, dextran is adhered to the barrier layer via ether linkage. Next, bromoacetic acid is reacted with the dextran matrix, thereby introducing a carboxymethyl group.

The following technique has been disclosed as techniques for immobilizing a physiologically active substance (e.g., protein or amino acid) having an amino group on the surface of the carboxymethyl-modified dextran produced based on this method. Namely, some carboxyl groups of the carboxymethyl-modified dextran are modified by treatment with an aqueous solution of N-hydroxysuccinimide (NHS) and N-(3-dimethylaminopropyl)-N'-ethylcarbodiimide (EDC) hydrochloric acid, so as to generate reactive ester functions, for example. Residual charges (that is, unreacted carboxyl groups) will contribute to the achievement of condensation of the physiologically active substance on a detection surface. By allowing an aqueous solution of a physiologically active substance (protein or amino acid) containing an amino group to come into contact with such detection surface, the physiologically active substance containing an amino group can be bound to a dextran matrix via covalent bonding.

Hydrogel produced by the above-mentioned method exerts excellent performance as the detection surface of a biosensor, because a physiologically active substance containing an amino group can be three-dimensionally immobilized. However, the method for producing hydrogel according to the above-mentioned method is problematic in that the method is complicated and the required production time is long. Furthermore, the method is also problematic in terms of safety because it requires the use of compounds such as epichlorohydrin or bromoacetic acid.

On the other hand, as a typical technique for immobilizing a physiologically active substance on a measurement chip, a method (amine coupling method) that involves binding an amino group of a physiologically active substance to a carboxyl group on a measurement chip is broadly used. This method requires dissolving a physiologically active substance in a buffer having a pH that is lower than the isoelectric point of such substance upon immobilization. Specifically, whereas a physiologically active substance will be positively charged when the pH is the isoelectric point or lower, the carboxyl group on a measurement chip are negatively charged from the alkali side to the acidic region of approximately pH 3.5. Therefore, a physiologically active substance is concentrated on a measurement chip due to electrostatic attraction. When such preconcentration does not occur, the immobilization amount of a physiologically active substance will drastically decrease. Thus, a physiologically active substance to be immobilized should be dissolved in a buffer having a pH that is lower than the isoelectric point of such substance, as disclosed in J. C. S. Chem. Commun., 1990, 1526 and U.S. Pat. No. 5,436,161.

This means that a physiologically active substance that is denatured under low-pH conditions is unable to be immobilized while maintaining its activity. Furthermore, a physiologically active substance such as an acidic protein has no positive net charge, even in the case of a pH of approximately 3.5. Thus, no preconcentration effects can be obtained, so that immobilization becomes impossible.

A physiologically active substance dissolved in a buffer having a pH that is higher than the isoelectric point can be immobilized on a solid surface because of electrostatic attraction between the substance and a cationic polymer immobilized on the solid surface. JP Patent Publication (Kokai) No. 8-245815 A (1996) discloses a technique using such principle, which involves alternately layering a protein and an organic polymer ion.

This method is very excellent in that a physiologically active substance can be conveniently immobilized. However, two problems arise in view of application to a biosensor. The first problem is that because binding between a protein and a substrate depends only on electrostatic interaction, a part of the physiologically active substances that have been electrostatically adsorbed on a solid surface may be dissociated due to a washing step using an acidic solution or an alkaline solution. The second problem is that a physiologically active substance is obtained as a densely packed monomolecular layer. In order to increase the immobilization amount of a physiologically active substance, it is desirable to three-dimensionally immobilize a physiologically active substance. Furthermore, dense packing of a physiologically active substance is not preferable in terms of application to a biosensor for measuring binding and dissociation behaviors of a compound interacting with a physiologically active substance.

Further, in the case of a measurement chip having a carboxyl group, such as a measurement chip having carboxymethyl dextran immobilized thereon as described in J. C. S. Chem. Commun., 1990, 1526, it is difficult to immobilize a protein, because preconcentration does not occur at pH 3.5 that is the acid dissociation constant of a carboxyl group, or lower.

In the amine coupling method as mentioned above, a measurement chip is previously coated with a polymer for protein immobilization and then a physiologically active substance is bound to the polymer. Thus, the physiologically active substance can be immobilized on the measurement chip. As a polymer for protein immobilization, a carboxymethylated (—$CH_2COOH$) polymer is known (U.S. Pat. No. 5,436,161, Colloids and Surfaces B: Biointerfaces, 1, 1993, 83-89; and Biosensors and Bioelectronics, 10, 1995, 813-822). However, this polymer has an anionic group in its molecule. Thus, the pH of a protein solution should be adjusted at the isoelectric point or lower, in order to immobilize a protein using charge concentration. Hence, an acidic protein should be immobilized in a low-pH region. Furthermore, such fluid is problematic in that it causes lower protein activity or death. Furthermore, when introduction of a cationic group into such polymer is attempted, a problem arises in that the cationic group and the carboxyl group that is a reactive group for protein immobilization form a salt and the polymer is gelatinized, so that the protein can not be immobilized.

DISCLOSURE OF THE INVENTION

An object of the present invention is to address the above-mentioned problems in conventional technology. Specifically, the first object of the present invention is to provide a biosensor and a production method therefor, by which hydrogel that enables immobilization of a physiologically active substance can be conveniently produced using safe raw materials. The second object of the present invention is to provide a biosensor and a method for immobilizing a physiologically active substance, by which preconcentration effects can be obtained at a pH that is the isoelectric point of a physiologically active substance or higher and the physiologically active substance can be covalently bound to the surface. The third object of the present invention is to provide a biosensor and a method for immobilizing a physiologically active substance, by which preconcentration effects can be obtained at pH 3.5 that is the acid dissociation constant of a carboxyl group or lower and the physiologically active substance can be bound to a surface via covalent bonding. The fourth object of the present invention is to provide an agent for immobilizing a physiologically active substance which can immobilize a physiologically active substance using charge concentration, even when the pH of a solution of a physiologically active substance such as a protein is the isoelectric point of said physiologically active substance or higher.

As a result of intensive studies to achieve the above objects, the present inventors have discovered that hydrogel that enables immobilization of a physiologically active substance can be conveniently produced through application of a polymeric hardener that has been developed for producing a silver halide photographic photosensitive material as a hydrophilic polymer having a reactive functional group capable of reacting with a hydroxyl group or an amino group of a physiologically active substance, that is, as hydrogel to be used for the detection surface of a biosensor. Further, the present inventors have discovered that by the use of a biosensor provided with a surface comprising a reactive group capable of chemically immobilizing a physiologically active substance and a cationic group, preconcentration effects can be obtained even when a solution containing a physiologically active substance and having a pH that is the isoelectric point of such substance or higher is used, and at the same time the physiologically active substance can be immobilized on the surface via covalent bonding. Further, the present inventors have discovered that, through the use of a biosensor provided with a surface comprising a reactive group capable of chemically immobilizing a physiologically active substance and an anionic group having an acid dissociation constant that is lower than that of a carboxyl group, preconcentration effects can be obtained even when a solution containing a physiologically active substance and having a pH lower than the acid dissociation constant (pKa=3.5) of a carboxyl group is used, and at the same time a physiologically active substance can be immobilized on a surface via covalent bonding. Further, the present inventors have discovered that a physiologically active substance can be immobilized using charge concentration by immobilizing a physiologically active substance on a substrate using a polymer having, within a molecule, a reactive group capable of chemically immobilizing the physiologically active substance and a cationic group, even when the pH of a solution of a physiologically active substance such as a protein is the isoelectric point of such substance or higher. The present invention has been completed based on these findings.

Thus, the first embodiment of the present invention provides a biosensor which comprises a substrate having a metal layer on its surface, wherein a hydrophilic polymer having a reactive functional group capable of reacting with a hydroxyl group or an amino group of a physiologically active substance is bound to the metal layer directly or indirectly via an intermediate layer.

Preferably, the reactive functional group of the hydrophilic polymer is a vinylsulfone group or a precursor thereof.

Preferably, the reactive functional group of the hydrophilic polymer is a dichlorotriazine group.

Preferably, the biosensor according to the present invention is obtained by forming a dense layer on the metal surface using an alkanethiol having a reactive group at its terminus or a disulfide that is an oxidized product of the alkanethiol, and then allowing the reactive group at the terminus of the alkanethiol to react with a hydrophilic polymer having a reactive functional group capable of reacting with a hydroxyl group or an amino group of a physiologically active substance.

Preferably, a carboxylic acid is introduced by allowing the reactive functional groups of the hydrophilic polymer to react with an amino acid.

Preferably, the film thickness of the intermediate layer is between 0.1 nm and 500 nm.

Preferably, the substrate is any of gold, silver, copper, platinum, and aluminum.

Preferably, the biosensor of the present invention is used in non-electrochemical detection, and more preferably in surface plasmon resonance analysis.

Another aspect of the present invention provides a method for producing the biosensor of the present invention as mentioned above, which comprises a step of chemically binding a hydrophilic polymer having a reactive functional group capable of reacting with a hydroxyl group or an amino group of a physiologically active substance to the surface of a substrate having a metal layer on its surface directly or indirectly via an intermediate layer.

Further another aspect of the present invention provides the biosensor according to the present invention, wherein a physiologically active substance is bound via covalent bonding to the reactive functional groups of the hydrophilic polymer or the carboxylic acid that has been introduced through the reaction of the reactive functional group with amino acid.

Further another aspect of the present invention provides a method for detecting or measuring a substance interacting with a physiologically active substance, which comprises a step of allowing a test substance to come into contact with the biosensor of the present invention to the surface of which the physiologically active substance binds via a covalent bond.

Preferably, the substance interacting with the physiologically active substance is detected or measured by a non-electrochemical method. More preferably, the substance interacting with the physiologically active substance is detected or measured by surface plasmon resonance analysis.

The second embodiment of the present invention provides a biosensor which comprises a surface having a reactive group capable of chemically immobilizing a physiologically active substance and a cationic group.

Preferably, the surface comprising a reactive group capable of chemically immobilizing a physiologically active substance and a cationic group is a surface having a water-soluble polymer bound thereto, a surface having a hydrophobic polymer bound thereto, or a surface having a self-assembling monolayer film formed thereon.

Preferably, the biosensor according to the present invention is obtained by coating a substrate with the polymer having a reactive group capable of chemically immobilizing a physiologically active substance and a cationic group.

Preferably, the reactive group capable of chemically immobilizing a physiologically active substance is a vinylsulfone group or a precursor thereof, a halotriazine group, an epoxy group, a carboxylic active ester group, an aldehyde group, an isocyanate group, or an acetoacetyl group.

Preferably, the cationic group is an onium or a precursor thereof.

Preferably, the surface comprising a reactive group capable of chemically immobilizing a physiologically active substance and a cationic group is formed on metal.

Preferably, the metal is any of gold, silver, copper, platinum, and aluminum.

Preferably, the biosensor of the present invention is used in non-electrochemical detection.

Preferably, the biosensor of the present invention is used in surface plasmon resonance analysis.

Another aspect of the present invention provides a method for immobilizing a physiologically active substance, which comprises allowing a solution containing a physiologically active substance and having a pH that is the isoelectric point or higher to come into contact with a surface having a reactive group capable of chemically immobilizing a physiologically active substance and a cationic group.

Preferably, the surface having a reactive group capable of chemically immobilizing a physiologically active substance and a cationic group is a surface of a biosensor.

Further another aspect of the present invention provides a method for detecting or measuring a substance interacting with a physiologically active substance, which comprises a step of allowing a test substance to come into contact with the biosensor of the present invention to the surface of which the physiologically active substance binds via a covalent bond.

Preferably, the substance interacting with the physiologically active substance is detected or measured by a non-electrochemical method.

Preferably, the substance interacting with the physiologically active substance is detected or measured by surface plasmon resonance analysis.

The third embodiment of the present invention provides a biosensor which comprises a surface having a reactive group capable of chemically immobilizing a physiologically active substance and an anionic group having an acid dissociation constant that is lower than that of a carboxyl group.

Preferably, the surface having a reactive group capable of chemically immobilizing a physiologically active substance and an anionic groups having an acid dissociation constant that is lower than that of a carboxyl group is a surface having a water-soluble polymer bound thereto, a surface having a hydrophobic polymer bound thereto, or a surface having a self-assembling monolayer film formed thereon.

Preferably, the biosensor according to the present invention is obtained by coating a substrate with a polymer having a reactive group capable of chemically immobilizing a physiologically active substance and an anionic group having an acid dissociation constant that is lower than that of a carboxyl group.

Preferably, the reactive group capable of chemically immobilizing a physiologically active substance is a vinylsulfone group or a precursor thereof, a halotriazine group, an epoxy group, a carboxylic active ester group, an aldehyde group, an isocyanate group, or an acetoacetyl group.

Preferably, the anionic group having an acid dissociation constant that is lower than that of a carboxyl group is a sulfuric ester group, a phosphoric ester group, or a sulfonic acid group.

Preferably, the surface having a reactive group capable of chemically immobilizing a physiologically active substance and an anionic group having an acid dissociation constant that is lower than that of a carboxyl group, is formed on metal.

Preferably, the metal is any of gold, silver, copper, platinum, and aluminum.

Preferably, the biosensor of the present invention is used in non-electrochemical detection.

Preferably, the biosensor of the present invention is used in surface plasmon resonance analysis.

Another aspect of the present invention provides a method for immobilizing a physiologically active substance, which comprises allowing a solution containing a physiologically active substance to come into contact with a surface having a reactive group capable of chemically immobilizing a physiologically active substance and an anionic group having an acid dissociation constant that is lower than that of a carboxyl group.

Preferably, the surface having a reactive group capable of chemically immobilizing a physiologically active substance and an anionic group having an acid dissociation constant that is lower than that of a carboxyl group, is a surface of biosensor.

Further another aspect of the present invention provides a method for detecting or measuring a substance interacting with a physiologically active substance, which comprises a step of allowing a test substance to come into contact with the biosensor of the present invention to the surface of which the physiologically active substance binds via a covalent bond.

Preferably, the substance interacting with the physiologically active substance is detected or measured by a non-electrochemical method.

Preferably, the substance interacting with the physiologically active substance is detected or measured by surface plasmon resonance analysis.

The fourth embodiment of the present invention provides an agent for immobilizing a physiologically active substance, which comprises a polymer having, within a molecule, a reactive group capable of chemically immobilizing a physiologically active substance and an cationic group.

Preferably, the reactive group capable of chemically immobilizing a physiologically active substance is a vinylsulfone group or a dichlorotriazine group.

Preferably, the cationic group is a primary amine salt, a secondary amine salt, a tertiary amine salt, or a quaternary ammonium compound.

Preferably, the polymer is a vinyl polymer.

Preferably, the polymer is obtained by copolymerization of acrylamide monomer or (meth)acrylamide monomer.

Preferably, the polymer is a polysaccharide or a derivative thereof.

Preferably, the polymer is a derivative of dextran.

Preferably, the polymer is a water-soluble polymer.

Preferably, the polymer has a number average molecular weight of 3000 or more.

Preferably, the agent for immobilizing a physiologically active substance according to the present invention is used for immobilizing a physiologically active substance using a solution containing a physiologically active substance and having a pH that is the isoelectric point or higher.

Another aspect of the present invention provides a method for immobilizing a physiologically active substance, which comprises allowing a physiologically active substance to come into contact with a substrate having the agent for immobilizing a physiologically active substance according to the present invention on its surface so as to chemically bind the physiologically active substance to the agent for immobilizing a physiologically active substance.

Preferably, a physiologically active substance is allowed to come into contact with a substrate using a solution containing the physiologically active substance and having a pH that is the isoelectric point or higher.

BEST MODE FOR CARRYING OUT THE INVENTION

Figure 1:
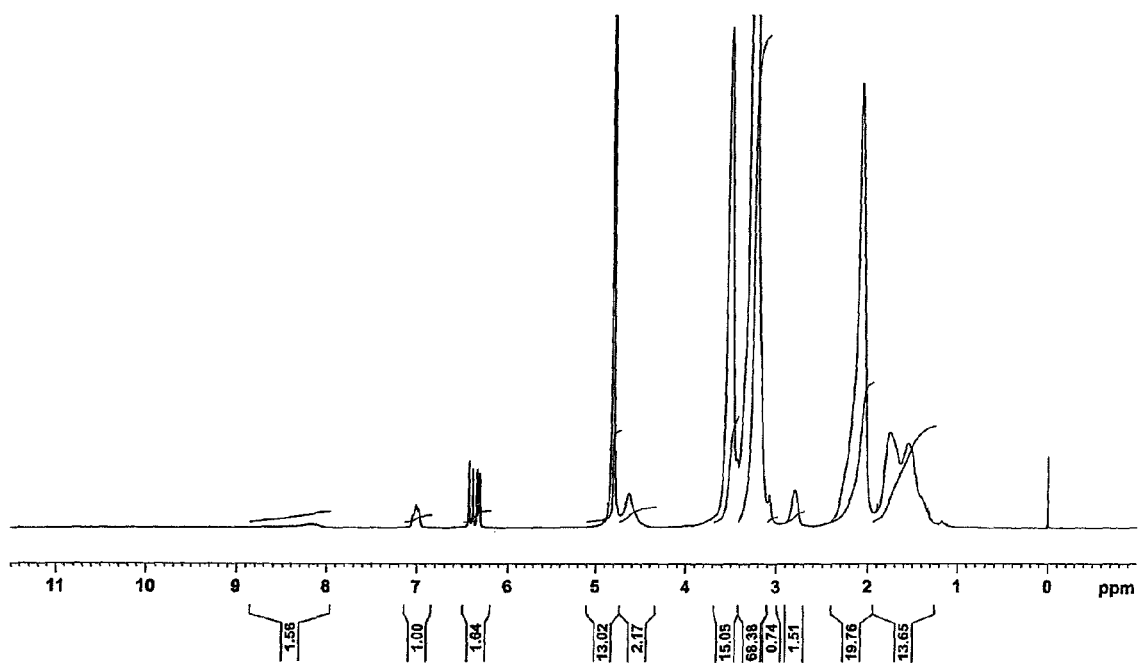
FIG. 1 shows the NMR chart of the polymer (P-1).

The embodiments of the present invention will be described below. Furthermore, in the present invention, when a numerical value represents the value of a physical property, the value of a characteristic, or the like, "(numerical value 1) to (numerical value 2)" means "(numerical value 1) or more and (numerical value 2) or less."

The biosensor of the present invention has as broad a meaning as possible, and the term biosensor is used herein to mean a sensor, which converts an interaction between biomolecules into a signal such as an electric signal, so as to measure or detect a target substance. The conventional biosensor is comprised of a receptor site for recognizing a chemical substance as a detection target and a transducer site for converting a physical change or chemical change generated at the site into an electric signal. In a living body, there exist substances having an affinity with each other, such as enzyme/substrate, enzyme/coenzyme, antigen/antibody, or hormone/receptor. The biosensor operates on the principle that a substance having an affinity with another substance, as described above, is immobilized on a substrate to be used as a molecule-recognizing substance, so that the corresponding substance can be selectively measured.

In the biosensor of the present invention, a metal surface or metal film can be used as a substrate. A metal constituting the metal surface or metal film is not particularly limited, as long as surface plasmon resonance is generated when the metal is used for a surface plasmon resonance biosensor. Examples of a preferred metal may include free-electron metals such as gold, silver, copper, aluminum or platinum. Of these, gold is particularly preferable. These metals can be used singly or in combination. Moreover, considering adherability to the above substrate, an interstitial layer consisting of chrome or the like may be provided between the substrate and a metal layer.

The film thickness of a metal film is not limited. When the metal film is used for a surface plasmon resonance biosensor, the thickness is preferably between 0.1 nm and 500 nm, and particularly preferably between 1 nm and 200 nm. If the thickness exceeds 500 nm, the surface plasmon phenomenon of a medium cannot be sufficiently detected. Moreover, when an interstitial layer consisting of chrome or the like is provided, the thickness of the interstitial layer is preferably between 0.1 nm and 10 nm.

Formation of a metal film may be carried out by common methods, and examples of such a method may include sputtering method, evaporation method, ion plating method, electroplating method, and nonelectrolytic plating method.

A metal film is preferably placed on a substrate. The description "placed on a substrate" is used herein to mean a case where a metal film is placed on a substrate such that it directly comes into contact with the substrate, as well as a case where a metal film is placed via another layer without directly coming into contact with the substrate. When a substrate used in the present invention is used for a surface plasmon resonance biosensor, examples of such a substrate may include, generally, optical glasses such as BK7, and synthetic resins. More specifically, materials transparent to laser beams, such as polymethyl methacrylate, polyethylene terephthalate, polycarbonate or a cycloolefin polymer, can be used. For such a substrate, materials that are not anisotropic with regard to polarized light and have excellent workability are preferably used.

According to the first embodiment of the present invention, the biosensor of the present invention is characterized in that it comprises a substrate having a metal layer on its surface, wherein a hydrophilic polymer having a reactive functional group capable of reacting with a hydroxyl group or an amino group of a physiologically active substance is bound to the metal layer directly or indirectly via an intermediate layer.

A polymeric hardener for silver halide photography can be used as a hydrophilic polymer that is used in the present invention and has a reactive functional group capable of reacting with hydroxyl groups or amino groups of a physiologically active substance. Polymeric hardeners that can be used in the present invention will be described as follows. A polymeric hardener is a polymer compound that has, within a molecule, a plurality of reactive functional groups that undergo binding reaction with a hydrophilic colloid such as gelatin. Such polymeric hardener is described in the following documents: JP Patent Publication (Kokai) No. 56-66841 A (1981), GB Patent No. 1,322,971, U.S. Pat. No. 3,671,256, JP Patent Publication (Kokai) No. 7-64226 A (1995), JP Patent Publication (Kokai) No. 7-140596 A (1995), JP Patent Publication (Kokai) No. 10-111545 A (1998), JP Patent Publication (Kokai) 2000-62629 A, JP Patent Publication (Kokai) No. 2004-20919 A, The Theory of the Photographic Process (written by James, 4$^{th}$ edition, page 84, 1977, Macmillan Publishers Limited), Polymeric Amine and Ammonium Salts (written by Campbelletal et al., pages 321 to 332, 1979, Pergamon Press, Ltd.), and the like.

A polymeric hardener that is used in the present invention is a polymer compound having a reactive functional group capable of binding to a functional group on the surface of a biosensor. Such polymeric hardener is preferably a polymer compound having a reactive functional group represented by the following formulae (1) to (9).

—SO$_2$CH=CH$_2$  Formula (1)

—SO$_2$CH$_2$CH$_2$X  Formula (2)

In formula (2), X is a group (e.g., —Cl, —OSO$_2$CH$_3$, —OSO$_2$C$_6$H$_4$—CH$_3$, —OCOCH$_3$, —OSO$_3^-$, or pyridinium) that is eliminated by substitution reaction or elimination reaction when the functional group represented by formula (2) reacts with a nucleophilic reagent or a base.

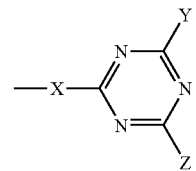

Formula (3)

In formula (3), X represents a single bond, —O—, or —NR— and R represents a hydrogen atom, an alkyl group, or an aralkyl group. Y and Z each represent a halogen atom (e.g., a chlorine atom or a bromine atom), an alkoxy group (e.g., methoxy), a hydroxyl group or a salt thereof, or an amino group that may be substituted. At least one of Y and Z is a halogen atom.

—CHO  Formula (4)

Formula (5):

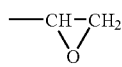

—NCO  Formula (6)

—NHCONHCOCH=CH$_2$  Formula (7)

—NHCONHCOCH$_2$CH$_2$X  Formula (8)

In the formula, X is as defined in formula (2).

—COX  Formula (9)

In the formula, X is a group (e.g., one of the following groups) that is easily eliminated when the functional group represented by formula (9) reacts with an amino group.

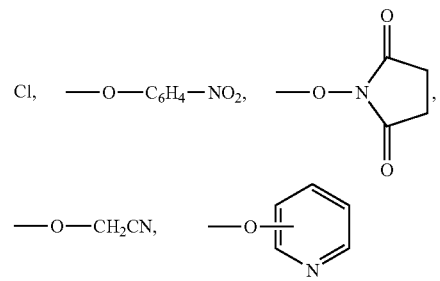

Formula (9) represents a group that is generally known as an active ester group or a mixed anhydride.

A polymerization method used upon production of a polymeric hardener that is used in the present invention is not particularly restricted. For example, such hardener can be produced by a condensation polymerization method. Furthermore, such hardener may also be produced by a method such as radical polymerization or anionic polymerization using compounds having ethylene unsaturated bonds. Furthermore, such hardener may also be produced by introducing the above reactive functional groups into natural polymers (e.g., starch, dextran, and gelatin). A method for introducing a functional group (functional groups represented by the above formulae (1) to (9) and hereinafter referred to as reactive functional groups) that are capable of reacting with a hydrophilic colloid that is used in the present invention is also not particularly restricted. A polymer may also be produced by performing polymerization reaction using monomers having a reactive functional group. Furthermore, a polymer may be previously produced and then the above reactive functional group may also be introduced by so-called polymer reaction. Furthermore, a method that involves performing polymerization reaction using a monomer compound having precursors of a reactive functional group and then generating a reactive functional group by an appropriate method is also effective.

A polymeric hardener that is used in the present invention may also be produced by radically polymerizing monomers having the above reactive functional group (or precursor thereof) and the ethylene unsaturated bond within the same molecule. Typical examples of monomers having a reactive functional group are compounds listed below.

   M-1

   M-2

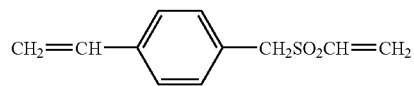   M-3

   M-4

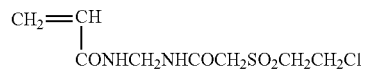   M-5

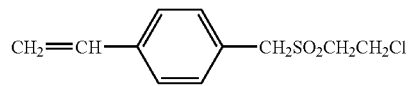   M-6

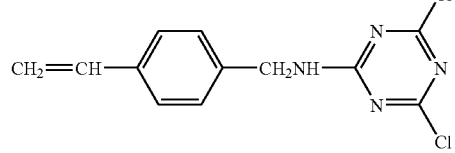   M-7

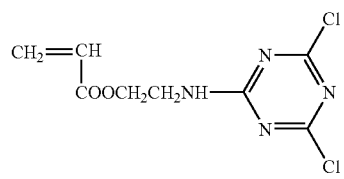   M-8

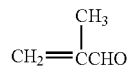   M-9

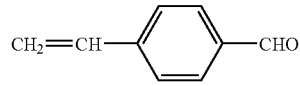   M-10

CH$_3$CH=CHCHO   M-11

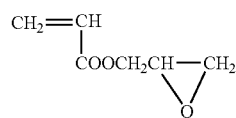   M-12

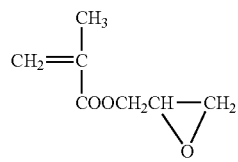   M-13

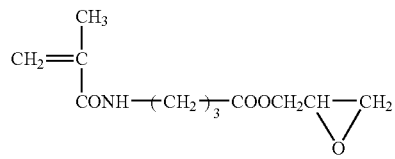   M-14

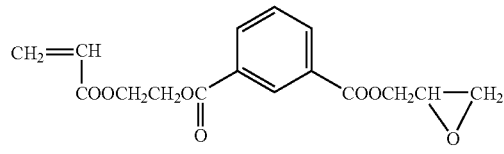   M-15

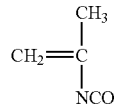   M-16

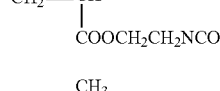   M-17

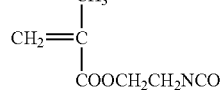   M-18

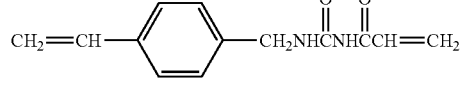   M-19

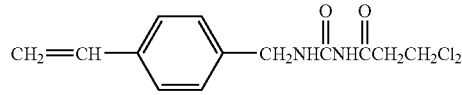   M-20

CH$_2$=CHCOCl   M-21

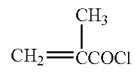   M-22

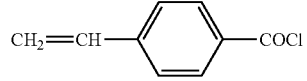   M-23

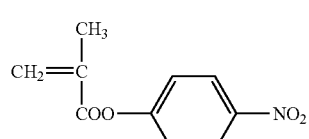   M-24

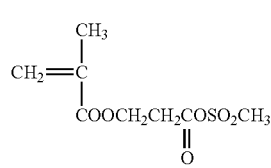   M-25

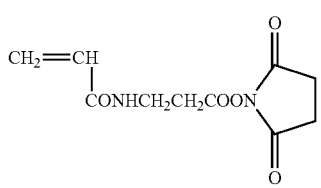

M-26

A polymer that is used in the present invention may be a homopolymer of a monomer having a reactive functional group, or a copolymer of such monomer and another one or two or more different types of monomer. In the case of such copolymer, the proportion of a monomer having a reactive functional group in such copolymer is 1 weight % or more and preferably 5 weight % or more. Radical copolymerization is not particularly limited, as long as the other monomer(s) are radically polymerizable. Specific examples of such monomer include monomers listed below. Furthermore, when the other monomer(s) have a functional group capable of undergoing reaction, it is preferable to select an appropriate combination of monomers within a range such that no reactions are caused to take place upon copolymerization with the functional groups represented by the above formulae (1) to (9).

Such specific examples are: acrylic acid, methacrylic acid, and the esters thereof (e.g., acrylic acid, methylacrylate, butylacrylate, benzylacrylate, hydroxyethylacrylate, $CH_2=CHCOO(CH_2CH_2O)_nR$ (where R is a hydrogen atom or an alkyl group and n is an integer of 1 or greater), methacrylic acid, methyl methacrylate, ethyl methacrylate, benzyl methacrylate, hydroxyethyl methacrylate, 2-ethylhexyl methacrylate, 2-methoxyethyl methacrylate, N,N-dimethylaminoethyl methacrylate, and 2-sulfoethyl methacrylate); amides of ethylene unsaturated carboxylic acid (e.g., acrylamide, methacrylamide, N-acryloyl morpholine, N,N-dimethylacrylamide, and 2-acrylamide-2-methylpropane sulfonate (or a salt thereof));
aromatic monomers (e.g., styrene, vinyltoluene, p-t-butylstyrene, p-vinylbenzoic acid, and vinylnaphthalene); and
other vinyl monomers (e.g., ethylene, propylene, vinyl chloride, vinylidene chloride, triphloroethylene, triphlorochloroethylene, vinyl acetate, vinyl propionate, vinyl alcohol, N-vinyl pyrrolidone, N-vinylacetoamide, acrylonitrile, and methacrylonitrile).

Specific examples of a polymeric hardener that is used in the present invention will be listed below, but the present invention is not limited by these examples. The copolymerization ratio of each compound represents a weight percentage.

P-1: M-1/2-acrylamide-2-methylpropane sodium sulfonate copolymer (10/90)
P-2: M-1/2-acrylamide-2-methylpropane sodium sulfonate copolymer (30/70)
P-3: M-1/2-acrylamide-2-methylpropane sodium sulfonate copolymer (50/50)
P-4: M-1/methylmethacrylate copolymer (20/80)
P-5: M-2/sodium acrylate copolymer (30/70)
P-6: M-2/2-hydroxyethyl methacrylate copolymer (20/80)
P-7: M-3/butylacrylate copolymer (60/40)
P-8: M-4/2-acrylamide-2-methylpropane sodium sulfonate copolymer (30/70)
P-9: M-6/ethylacrylate copolymer (60/40)
P-10: M-7/N-vinyl pyrrolidone copolymer (20/80)
P-11: M-7/diacetoneacrylamide copolymer (10/90)
P-12: M-10/sodium methacrylate copolymer (15/85)
P-13: M-10/methylacrylate/methylmethacrylate copolymer (20/40/40)
P-14: M-12/ethyl methacrylate copolymer (33/67)
P-15: M-12/2-acrylamide-2-methylpropane sodium sulfonate copolymer (15/85)
P-16: M-13/methyl methacrylate copolymer (33/67)
P-17: M-13/2-acrylamide-2-methylpropane sodium sulfonate copolymer (20/80)
P-18: M-13/N-acryloyl morpholine copolymer (20/80)
P-19: M-13/methoxypolyethylene glycol (23 mer) monomethacrylate copolymer (50/50)
P-20: M-18/N,N-dimethylacrylamide copolymer (5/95)
P-21: M-18/butylmethacrylate copolymer (30/70)
P-22: M-18/styrene/butylacrylate copolymer (20/30/50)
P-23: M-19/2-acrylamide-2-methylpropane sodium sulfonate copolymer (20/80)
P-24: M-23/methylacrylate copolymer (20/80)
P-25: M-24/ethylacrylate/styrene copolymer (20/50/30)
P-26: M-26/acrylamide copolymer (25/75)
P-27: M-26/N,N-dimethylaminoethyl methacrylate copolymer (30/70)

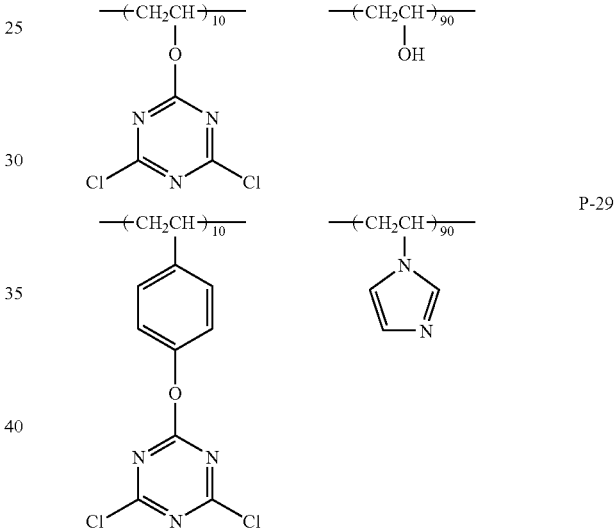

As a polymeric hardener having a reactive functional group, which is used in the present invention, preferably, an active olefin type polymeric hardener, an s-triazine type polymeric hardener, an active halogen type polymeric hardener, an aldehyde type polymeric hardener, a glycidyl type polymeric hardener, or the like is used. Further preferably, an active olefin type polymeric hardener or a precursor thereof, an s-triazine type polymeric hardener, or a glycidyl type polymeric hardener is used. A vinylsulfone type polymeric hardener, a precursor thereof, or a dichlorotriazine type polymeric hardener is particularly preferable.

A polymeric hardener in the present invention is immobilized on the surface of a biosensor, in order to form hydrogel. Accordingly, it is desirable that such polymer have hydrophilic groups other than the reactive functional groups. Specific examples of such hydrophilic groups include nonionic groups such as a hydroxyl group and an ethylene glycol group, anionic groups such as a sulfonic acid group, a carboxylic acid group, and a phosphoric acid group, cationic groups such as a quaternary ammonium group and a pyridinium group, and dipolar ionic groups such as a phosphorylcholine group.

Examples of monomer units having a hydrophilic group in the present invention include the following monomers:

monomers having an nonionic group (e.g., 2-hydroxyethylacrylate, 2-hydroxyethyl methacrylate, hydroxypropyl acrylate, hydroxypropylmethacrylate, 2-hydroxy-3-chloropropylacrylate, β-hydroxyethyl β'-acryloyloxyethylphthalate, 1,4-butylene glycol monoacrylate, hydroxystyrene, allylalcohol, methallyl alcohol, isopropenyl alcohol, and 1-butenyl alcohol);

monomers having an anionic group (e.g., vinyl sulfonic acid, methallylsulfonic acid, 2-acrylamide-2-methylpropane sulfonic acid, sulfoethyl methacrylate, styrenesulfonic acid, acrylic acid, methacrylic acid, and 2-(phosphonoethyloxy) ethyl methacrylate);

monomers having a cationic group (e.g., [2-(acryloyloxy) ethyl]trimethyl ammonium chloride and [2-(methacryloyloxy)ethyl]trimethyl)ammonium chloride; and monomers having a dipolar ionic group (e.g., [2-(methacryloyloxy)ethyl]dimethyl-(3-sulfopropyl)ammonium hydroxide and [2-(methacryloyloxy)ethyl]phosphorylcholine).

Introduction of cationic group or anionic group into a polymeric hardener enables concentration of a physiologically active substance having opposite charge on a detection surface using electrostatic interaction. For example, in the case of a protein that has been dissolved in a buffer with a pH higher than the isoelectric point, the protein is electrostatically concentrated on the hydrogel surface to which a polymeric hardener having a cationic group has been bound. Thus, it becomes possible to efficiently bind the protein to the reactive functional group. In contrast, in the case of protein that has been dissolved in a buffer with a pH lower than the isoelectric point, the protein is electrostatically concentrated on the hydrogel surface to which a polymeric hardener having an anionic group has been bound. Thus, it also becomes possible to efficiently bind the protein to reactive functional groups.

In the present invention, any known technique can be used as a method for binding a polymeric hardener that is a binding matrix to the metal surface. Examples of methods that can be applied herein include a method that involves binding a binding matrix to the metal surface via a hydrophobic polymer (see JP Patent Publication (Kokai) No. 2004-271514 A and JP Patent Application No. 2004-225130)) and a method that involves binding a binding matrix to the metal surface via a densely packed monolayer of X—R—Y (where X binds to metal and Y binds to the binding matrix) as disclosed in Japanese Patent No. 2815120. A preferable method involves forming a dense layer on the metal surface using alkanethiol (or an oxidized product thereof; that is, disulfide) having a reactive group at terminus and then allowing the reactive groups at the terminus of alkanethiol to react with a polymeric hardener.

By allowing a physiologically active substance to come into contact with a biosensor surface in the present invention, the reactive functional group of a polymeric hardener covalently bind to the physiologically active substance. Thus, it becomes possible to immobilize the physiologically active substance on the biosensor. Furthermore, by allowing an amino acid solution to come into contact with the biosensor surface, the reactive functional group of a polymeric hardener react with an amino group of the amino acid. As a result, the reactive functional group is converted to carboxylic acid. The biosensor surface having carboxylic acid can be activated by a known method (e.g., by the use of water-soluble carbodiimide, 1-(3-Dimethylaminopropyl)-3 ethylcarbodiimide (EDC), and N-Hydroxysuccinimide (NHS)). Thus, it becomes possible to immobilize a physiologically active substance having an amino group on the surface. Examples of techniques for activating carboxylic acid, which can also be preferably used, include a method disclosed in JP Patent Application No. 2004-238396 (where specifically, such method involves activating carboxyl groups existing on the substrate surface by the use of a uronium salt, a phosphonium salt, or a triazine derivative which has a specific structure, so as to form carboxamide groups) and a method disclosed in JP Patent Application No. 2004-275012 (where specifically, the method involves activating carboxyl groups existing on the substrate surface by the use of a carbodiimide derivative or a salt thereof, forming ester by the use of a nitrogen-containing heteroaromatic compound having hydroxyl groups, a phenol derivative having electron-withdrawing groups, or an aromatic compound having thiol groups, and then performing reaction with amine, thereby forming carboxamide groups).

In the present invention, the hydrophilic polymer having a reactive functional group capable of reacting with a hydroxyl group or an amino group of a physiologically active substance is bound to the metal layer directly or indirectly via an intermediate layer. As the intermediate layer, a hydrophobic polymer or a self-assembling membrane can be used. The hydrophobic polymer and the self-assembling membrane are described below.

A hydrophobic polymer used in the present invention is a polymer having no water-absorbing properties. Its solubility in water (25° C.) is 10% or less, more preferably 1% or less, and most preferably 0.1% or less.

A hydrophobic monomer which forms a hydrophobic polymer can be selected from vinyl esters, acrylic esters, methacrylic esters, olefins, styrenes, crotonic esters, itaconic diesters, maleic diesters, fumaric diesters, allyl compounds, vinyl ethers, vinyl ketones, or the like. The hydrophobic polymer may be either a homopolymer consisting of one type of monomer, or copolymer consisting of two or more types of monomers.

Examples of a hydrophobic polymer that is preferably used in the present invention may include polystyrene, polyethylene, polypropylene, polyethylene terephthalate, polyvinyl chloride, polymethyl methacrylate, polyester, and nylon.

A substrate is coated with a hydrophobic polymer according to common methods. Examples of such a coating method may include spin coating, air knife coating, bar coating, blade coating, slide coating, curtain coating, spray method, evaporation method, cast method, and dip method.

In the dip method, coating is carried out by contacting a substrate with a solution of a hydrophobic polymer, and then with a liquid which does not contain the hydrophobic polymer. Preferably, the solvent of the solution of a hydrophobic polymer is the same as that of the liquid which does not contain said hydrophobic polymer.

In the dip method, a layer of a hydrophobic polymer having an uniform coating thickness can be obtained on a surface of a substrate regardless of inequalities, curvature and shape of the substrate by suitably selecting a coating solvent for hydrophobic polymer.

The type of coating solvent used in the dip method is not particularly limited, and any solvent can be used so long as it can dissolve a part of a hydrophobic polymer. Examples thereof include formamide solvents such as N,N-dimethylformamide, nitrile solvents such as acetonitrile, alcohol solvents such as phenoxyethanol, ketone solvents such as 2-butanone, and benzene solvents such as toluene, but are not limited thereto.

In the solution of a hydrophobic polymer which is contacted with a substrate, the hydrophobic polymer may be dissolved completely, or alternatively, the solution may be a suspension which contains undissolved component of the hydrophobic polymer. The temperature of the solution is not particularly limited, so long as the state of the solution allows a part of the hydrophobic polymer to be dissolved. The temperature is preferably −20° C. to 100° C. The temperature of the solution may be changed during the period when the substrate is contacted with a solution of a hydrophobic polymer. The concentration of the hydrophobic polymer in the solution is not particularly limited, and is preferably 0.01% to 30%, and more preferably 0.1% to 10%.

The period for contacting the solid substrate with a solution of a hydrophobic polymer is not particularly limited, and is preferably 1 second to 24 hours, and more preferably 3 seconds to 1 hour.

As the liquid which does not contain the hydrophobic polymer, it is preferred that the difference between the SP value (unit: $(J/cm^3)^{1/2}$) of the solvent itself and the SP value of the hydrophobic polymer is 1 to 20, and more preferably 3 to 15. The SP value is represented by a square root of intermolecular cohesive energy density, and is referred to as solubility parameter. In the present invention, the SP value δ was calculated by the following formula. As the cohesive energy (Ecoh) of each functional group and the mol volume (V), those defined by Fedors were used (R. F. Fedors, Polym. Eng. Sci., 14(2), P147, P472 (1974)).

$$\Delta = (\Sigma Ecoh/\Sigma V)^{1/2}$$

Examples of the SP values of the hydrophobic polymers and the solvents are shown below;
Solvent: 2-phenoxyethanol: 25.3 against polymethylmethacrylate-polystyrene copolymer (1:1): 21.0
Solvent: acetonitrile: 22.9 against polymethylmethacrylate: 20.3
Solvent: toluene: 18.7 against polystyrene: 21.6

The period for contacting a substrate with a liquid which does not contain the hydrophobic polymer is not particularly limited, and is preferably 1 second to 24 hours, and more preferably 3 seconds to 1 hour. The temperature of the liquid is not particularly limited, so long as the solvent is in a liquid state, and is preferably −20° C. to 100° C. The temperature of the liquid may be changed during the period when the substrate is contacted with the solvent. When a less volatile solvent is used, the less volatile solvent may be substituted with a volatile solvent which can be dissolved in each other after the substrate is contacted with the less volatile solvent, for the purpose of removing the less volatile solvent.

The coating thickness of a hydrophobic polymer is not particularly limited, but it is preferably between 0.1 nm and 500 nm, and particularly preferably between 1 nm and 300 nm.

Next, the self-assembling membrane is described. Sulfur compounds such as thiol and disulfides are spontaneously adsorbed onto a noble metal substrate such as gold, providing a monomolecular-sized ultra thin film. Furthermore, such assembly is referred to as a self-assembling membrane, because it is shown to have sequences depending on the crystal lattice of a substrate or the molecular structure of adsorbed molecules. Examples of self-assembling compounds which can be used in the present invention include 7-carboxy-1-heptanethiol, 10-carboxyl-decanethiol, 4,4'-dithiobutyric acid, and 11-hydroxy-1-undecanethiol, 11-amino-1-undecanethiol.

According to the second embodiment of the present invention, the biosensor of the present invention is characterized in that it comprises a surface having a reactive group capable of chemically immobilizing a physiologically active substance and a cationic group.

The reactive group capable of chemically immobilizing a physiologically active substance is not particularly limited, as long as it can react with an amino group, a thiol groups, a hydroxyl groups or a carboxyl group of a protein, for example, and do not react with the cationic group listed below. Specific examples of the above reactive group include those listed in the following Table 1.

TABLE 1

| Immobilization group type | Reaction scheme with physiologically active substance |
|---|---|
| Acetoacetyl | 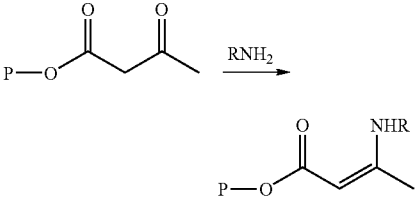 |
| Epoxy | 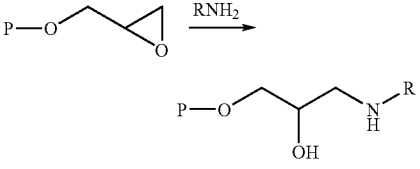 |
| Oxetane | 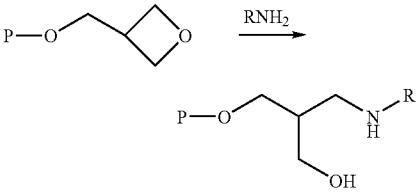 |
| Epoxy | 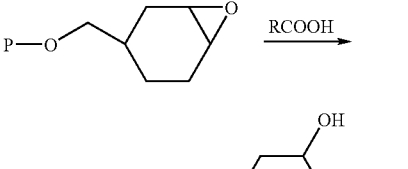 |
| Aziridine | 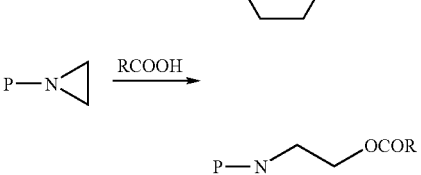 |
| Methylacrylamide glycolate ether | 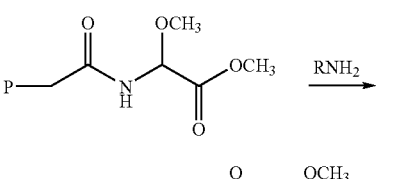 |

TABLE 1-continued

| Immobilization group type | Reaction scheme with physiologically active substance |
|---|---|
| Carbodiimide | P—N=C=N—R'  $\xrightarrow{RCOOH}$  P—NH—C(=O)—N(R')—COR |
| Carbonate | P—O—CH2—(cyclic carbonate)  $\xrightarrow{RNH_2}$  P—O—CH2—CH(OH)—CH2—OCONHR |
| Vinylsulfone | P—CH2—S(=O)2—CH=CH2  $\xrightarrow{RNH_2}$  P—CH2—S(=O)2—CH2CH2—NHR |
| Chlorotriazine | P—NH—(triazine-Cl2)  $\xrightarrow{RNH_2}$  P—NH—(triazine-Cl-NHR) |
| Urethane | P—NH—C(=O)—O—C6H4—NO2  $\xrightarrow{RNH_2}$  P—NH—C(=O)—NHR |

The reactive group capable of chemically immobilizing a physiologically active substance is preferably a vinylsulfone group or a precursor thereof, a halotriazine group, an epoxy group, a carboxylic active ester group, an aldehyde group, an isocyanate group, or an acetoacetyl group. In view of storage stability and the strength of the reactivity with an amino group at a high-pH region, such reactive group is more preferably a vinylsulfone group or a precursor thereof, or a dichlorotriazine group, and is particularly preferably a vinylsulfone group.

The cationic group is not particularly limited, as long as it is positively charged and do not react with the reactive group. Specific examples of the cationic group include oniums and the precursors thereof. Examples of the cationic group specifically include primary to tertiary amine salts, primary to quaternary ammonium compounds, pyridinium salts, phosphonium salts, oxonium salts, sulfonium salts, and imidazolium salts. Of these, primary to tertiary amine salts, primary to quaternary ammonium compounds, pyridinium salts, and imidazolium salts are preferable. More preferable examples of the same include primary to tertiary amine salts and quaternary ammonium compounds.

The surface having a reactive group capable of chemically immobilizing a physiologically active substance and a cationic group is preferably a self-assembling monolayer surface, a hydrophobic polymer-bound surface, or a water-soluble polymer-bound surface.

A self-assembling monolayer will be explained. Sulfur compounds such as thiol and disulfides are spontaneously adsorbed onto a noble metal substrate such as gold, providing a monomolecular-sized ultra thin film. Furthermore, such assembly is referred to as a self-assembling film, because it is shown to have sequences depending on the crystal lattice of a substrate or the molecular structure of admolecules. Examples of such self-assembling monolayer film include alkanethiols on gold surfaces, alkylsilanes on glass surfaces, and alcohols on silicon surfaces. Specific examples of alkanethiols that can be used herein include 7-carboxy-1-heptanethiol, 10-carboxyl-decanethiol, 4,4'-dithiobutyric acid, and 11-hydroxy-1-undecanethiol, 11-amino-1-undecanethiol. These self-assembling monolayer is formed of a compound having a reactive group capable of chemically immobilizing a physiologically active substance and a compound having a cationic group, making it possible to preconcentrate a physiologically active substance with a pH that is the isoelectric point or higher onto a two-dimensional surface and bind it thereto.

The hydrophobic polymer compound that can be used in the present invention is generally a polymer compound having no water-absorbing properties or having low water-absorbing properties. The solubility of such compound in water (25° C.) is preferably 10% or less, more preferably 1% or less, and most preferably 0.1% or less.

Specific examples of the hydrophobic polymer include a polyacrylic acid derivative, a polymethacrylic acid derivative, polyethylene (PE), polypropylene (PP), polybutadiene, polymethylpentene, cycloolefin polymer, polystyrene (PS), acrylonitrile/butadiene/styrene copolymer (ABS), styrene/maleic anhydride copolymer/polyvinyl chloride (PVC), polyethylene terephthalate (PET), polyethylene naphthalate (PEN), nylon 6, nylon 66, cellulose acetate (TAC), polycarbonate (PC), modified polyphenylene ether (m-PPE), polyphenylene sulfide (PPS), polyether ketone (PEK), polyether ether ketone (PEEK), polysulfone (PSF), polyether sulfone (PES), polyphenylene sulfide (PPS), and liquid crystal polymer (LCP). Preconcentration and binding of a physiologically active substance with a pH that is the isoelectric point or higher to a two-dimensional surface are also made possible, when a reactive group capable of chemically immobilizing a physiologically active substance and a cationic group are introduced on the surfaces of the above-mentioned hydrophobic polymer.

Coating of a substrate with a hydrophobic polymer compound can also be performed by a standard method such as spin coating, air knife coating, bar coating, blade coating, slide coating, and curtain coating methods, a spray method, a vacuum evaporation method, a cast method, and a dip method.

Examples of a water-soluble polymer include natural polymers such as a dextran derivative, a starch derivative, a cellulose derivative, and gelatin, and synthetic polymers such as polyvinyl alcohol, polyethylene glycol, polyvinyl pyrrolidone, a polyacrylamide derivative, and polymethylvinylether. When a cationic group is introduced at a high rate, the previously described hydrophobic polymers will become water-soluble polymers. In view of application to a biosensor, natural water-soluble polymers are preferable, and a dextran derivative is particularly preferable.

The water-soluble polymer bound to a surface forms three-dimensional hydrogel. Introduction of a reactive functional group into such three-dimensional hydrogel enables three-dimensional immobilization of a physiologically active substance as disclosed in U.S. Pat. No. 5,436,161. Compared with two-dimensional immobilization on a surface, three-dimensional immobilization is extremely advantageous in view of application to a biosensor, because the binding amount of a physiologically active substance is increased. Based on such viewpoint, it is preferable in the present invention to immobilize a physiologically active substance using a surface on which a water-soluble polymer having a reactive group capable of chemically immobilizing a physiologically active substance and a cationic group has been bound; that is, using three-dimensional hydrogel having a reactive group capable of chemically immobilizing a physiologically active substance and a cationic group.

Furthermore, a hydrophobic polymer compound and a water-soluble polymer that can be used in the present invention may be a synthetic polymer compound, or a natural polymer or a derivative thereof.

As a synthetic polymer compound that can be used in the present invention, a compound known as a polymeric hardener for silver salt photography can be used. Polymeric hardeners having a cationic group and a reactive group such as P-5, P-13, P-14, and P-20 disclosed in JP Patent Publication (Kokai) No. 60-61742 A (1985) can be preferably used in the present invention.

A method for introducing a functional group into a polymer that is used in the present invention is also not particularly restricted. A polymer may be produced by performing a copolymerization reaction between a monomer having a reactive functional group and a monomer having a cationic group. Alternatively, a polymer may be previously produced and then the above reactive functional group and the cationic group may be introduced by a so-called polymer reaction. Furthermore, a method that involves performing copolymerization reaction using a monomer compound having precursors of a reactive functional group and a cationic group and then generating the reactive functional group by an appropriate method is also effective. A polymer that is used in the present invention may also be produced by copolymerization of other (different) monomer components, in addition to a monomer component having a reactive functional group and a monomer component having a cationic group.

Examples of such other monomer components that are used in the present invention other than a monomer component having a reactive functional group and a monomer component having a cationic group include the following monomers:

acrylic esters, methacrylic acid esters, and amides of ethylene unsaturated carboxylic acid (e.g., acrylamide, methacrylamide, N-acryloyl morpholine, and N,N-dimethylacrylamide, 2-acrylamide-2-methylpropane sulfonic acid (or a salt thereof));

aromatic monomers (e.g., styrene, vinyltoluene, p-t-butylstyrene, and vinylnaphthalene); other vinyl monomers (e.g., ethylene, propylene, vinyl chloride, vinylidene chloride, triphloroethylene, triphlorochloroethylene, vinyl acetate, vinyl propionate, vinyl alcohol, N-vinyl pyrrolidone, N-vinyl acetoamide, acrylonitrile, and methacrylonitrile);

monomers having an nonionic group (e.g., 2-hydroxyethylacrylate, 2-hydroxyethyl methacrylate, hydroxypropylacrylate, hydroxypropylmethacrylate, 2-hydroxy-3-chloropropylacrylate, β-hydroxyethyl-β'-acryloyloxyethylphthalate, 1,4-butylene glycol monoacrylate, hydroxystyrene, allylalcohol, methallyl alcohol, isopropenyl alcohol, and 1-butenyl alcohol); and monomers having a dipolar ionic group (e.g., [2-(methacryloyloxy)ethyl]dimethyl-(3-sulfopropyl)ammonium hydroxide and [2-(methacryloyloxy)ethyl]phosphorylcholine).

Examples of a natural polymer or a derivative thereof that can be used in the present invention include dextran, cellulose, guar gum, starch, hydroxyethyl dextran, hydroxyethyl cellulose, hydroxyethyl guar gum, hydroxyethyl starch, methyl dextran, methyl cellulose, methyl guar gum, methyl starch, ethyl dextran, ethyl cellulose, ethyl guar gum, ethyl starch, hydroxypropyl dextran, hydroxypropyl cellulose, hydroxypropyl guar gum, hydroxypropyl starch, hydroxyethylmethyl cellulose, hydroxyethylmethyl guar gum, hydroxyethylmethyl starch, hydroxypropylmethyl cellulose, hydroxypropylmethyl guar gum, and hydroxypropylmethyl starch. Of these, dextran, hydroxyethyl dextran, hydroxypropyl dextran, cellulose, hydroxyethyl cellulose, and hydroxypropyl cellulose are preferable. Furthermore, a substituent of such polysaccharide, such as a hydroxyethyl group and a hydroxypropyl group, may have been substituted with a single substituent or with a plurality of substituents. The substitution degree per unit of constitutive monosaccharide residue ranges from 0.1 to 3.0 and particularly preferably ranges from 0.5 to 1.5. Furthermore, the weight average molecular weights of these polysaccharides or the derivatives thereof range from 10,000 to 10,000,000 and particularly preferably range from 100,000 to 1,000,000.

A natural polymer or a derivative thereof having a cationic group introduced therein can also be obtained by synthesis using a known method, such as a method disclosed in JP Patent Publication (Kokai) No. 57-5701 A (1982). Furthermore, commercial cationic polysaccharides can also be used. Examples of such commercial cationic polysaccharides include a cationic cellulose derivative, a cationic guar gum derivative, and a cationic dextran derivative. Specific examples of such cationic cellulose derivative include polymer JR-30M, polymer JR-400, and polymer JR-125 (all produced by Union Carbide Corporation), Cellcoat L-200 and Cellcoat H-100 (all produced by National Starch and Chemical Company), and Poise C-60H, Poise C-80M, and Poise C-150L (all produced by Kao Corporation). Specific examples of such cationic guar gum derivative include JAGUAR C13S, JAGUAR C15, and JAGUAR C17 (all produced by Meyhall Chemical AG). Specific examples of such cationic dextran derivative include CDC, CDC-L, CDC-H, and CDC-NK (all produced by Meito Sangyo. Co., Ltd.).

Through introduction of a reactive group such as a vinylsulfone group, a dichlorotriazine group, and an epoxy group into these cationic polysaccharides, a polymer (an agent for immobilizing a physiologically active substance) that is used in the present invention can be synthesized. A known method can be used as a method for introducing a reactive functional group into a natural polymer or a derivative thereof. For example, when an acetoacetyl group is introduced into polysaccharides, a method that involves dissolving polysaccharides in a good solvent such as dimethylformamide and then adding a diketene gas, a method that involves adding a diketene gas to powders of polysaccharides, a method that involves allowing polysaccharides to react with acetoacetic ester in a solution to perform transesterification, and the like are used. Regarding other methods for introducing a eactive functional group, a method disclosed in JP Patent Application No. 2005-46977 can preferably be used.

Specific examples of a polymer having a reactive group capable of chemically immobilizing a physiologically active substance and a cationic group include the following specific compound (P-1) and the like.

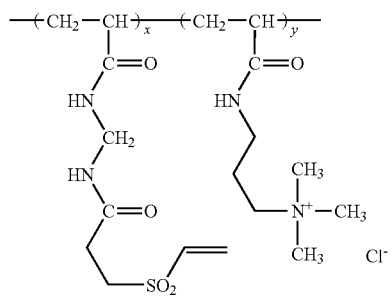

According to the present invention, a method for immobilizing a physiologically active substance is provided, which comprises allowing a solution containing a physiologically active substance and having a pH that is the isoelectric point or higher to come into contact with a surface having a reactive group capable of chemically immobilizing a physiologically active substance and a cationic group as mentioned above. With the above immobilization method of the present invention, since a cationic group has been introduced on a surface, preconcentration effects (whereby a physiologically active substance is concentrated on the surface of a measurement chip due to electrostatic attraction) can be obtained, even when a solution containing the physiologically active substance and having a pH that is the isoelectric point or higher is allowed to come into contact with the surface.

In the biosensor obtained as mentioned above, a physiologically active substance is covalently bound via the reactive functional group capable of chemically immobilizing a physiologically active substance which exists on the surface, so that the physiologically active substance can be immobilized on the metal surface or metal film.

According to the third embodiment of the present invention, the biosensor of the present invention is characterized in that it comprises a surface having a reactive group capable of chemically immobilizing a physiologically active substance and an anionic group having an acid dissociation constant that is lower than that of a carboxyl group.

As the reactive group capable of chemically immobilizing a physiologically active substance, those as mentioned herein above can be preferably used. The preferred examples of the reactive group capable of chemically immobilizing a physiologically active substance include a vinylsulfone group or a precursor thereof, a halotriazine group, an epoxy group, a carboxylic active ester group, an aldehyde group, an isocyanate group, or an acetoacetyl group. In view of the strength of the reactivity at a low-pH region, a carboxylic active ester group is more preferable.

Carboxylic active ester has high reactivity, so that hydrolysis gradually takes place in the presence of water. Accordingly, polymer synthesis is associated with difficulty when it is prepared by polymerization of monomers containing carboxylic active ester. Hence, it is preferable to perform, as a first step, the synthesis of a polymer containing carboxylic acid and then to covert the carboxyl group to an active ester immediately before or after the binding of the polymer to a surface.

A known method can be used as a method for activating a carboxyl group. For example, a method by which carboxyl groups are activated using 1-(3-Dimethylaminopropyl)-3 ethylcarbodiimide (EDC) (water-soluble carbodiimide) and N-Hydroxysuccinimide (NHS) can be used. Furthermore, a method disclosed in JP Patent Application No. 2004-238396 (where specifically, the method for forming carboxamide groups involves activating carboxyl groups that exist on the surface of a substrate using a uronium salt, a phosphonium salt, or a triazine derivative having a specific structure) and a method disclosed in JP Patent Application No. 2004-275012 (where specifically, the method for forming carboxamide groups involves activating carboxyl groups that exist on the surface of a substrate using a carbodiimide derivative or a salt thereof, converting the activated carboxyl groups to ester using a nitrogen-containing heteroaromatic compound having a hydroxyl group, a phenol derivative having an electron-withdrawing group, or an aromatic compound having a thiol group, and then allowing the ester to react with amine) can also be preferably used.

Preferred examples of the anionic group having an acid dissociation constant that is lower than that of a carboxyl group include a sulfuric ester group, a phosphoric ester group, and a sulfonic acid group. In view of chemical stability, a sulfonic acid group is more preferable.

The surface having a reactive group capable of chemically immobilizing a physiologically active substance and an anionic groups having an acid dissociation constant that is lower than that of a carboxyl group is preferably a self-assembling monolayer surface, a hydrophobic polymer-bound surface, or a water-soluble polymer-bound surface.

The self-assembling monolayer is as mentioned herein above. These self-assembling monolayer is formed of a compound having a reactive group capable of chemically immobilizing a physiologically active substance and a compound having an anionic groups having an acid dissociation constant that is lower than that of a carboxyl group, making it possible to pre-concentrate a physiologically active substance onto a two-dimensional surface and bind it thereto.

The hydrophobic polymer compound is also as mentioned herein above. When a reactive group capable of chemically immobilizing a physiologically active substance and a compound having an anionic groups having an acid dissociation constant that is lower than that of a carboxyl group are introduced on the surface of the hydrophobic polymer, a physiologically active substance can be pre-concentrated onto a two-dimensional surface, and can be bound thereto.

Examples of a water-soluble polymer include natural polymers such as a dextran derivative, a starch derivative, a cellulose derivative, and gelatin, and synthetic polymers such as polyvinyl alcohol, polyethylene glycol, polyvinyl pyrrolidone, a polyacrylamide derivative, and polymethylvinylether. When a cationic group is introduced at a high rate, the previously described hydrophobic polymers will become water-soluble polymers. In view of application to a biosensor, natural water-soluble polymers are preferable, and a dextran derivative is particularly preferable.

The water-soluble polymer is also as mentioned herein above. It is preferable in the present invention to immobilize a physiologically active substance using a surface on which a water-soluble polymer having a reactive group capable of chemically immobilizing a physiologically active substance and an anionic groups having an acid dissociation constant that is lower than that of a carboxyl group has been bound;

that is, using three-dimensional hydrogel having a reactive group capable of chemically immobilizing a physiologically active substance and an anionic groups having an acid dissociation constant that is lower than that of a carboxyl group.

Furthermore, a hydrophobic polymer compound and a water-soluble polymer that can be used in the present invention may be a synthetic polymer compound, or a natural polymer or a derivative thereof.

Upon production of a polymer (that is used in the present invention) having a reactive functional group (hereinafter, referred to as a reactive functional group) capable of covalently binding to amino groups and having an anionic group (hereinafter referred to as an anionic group) that have a pKa value lower than that of carboxylic acid, a polymerization method therefor is not particularly restricted. For example, such polymer may be produced by a condensation polymerization method or radical polymerization using compounds having ethylene unsaturated bonds, or anionic polymerization method. Furthermore, such polymer may also be synthesized using a natural polymer (e.g., a natural polysaccharide such as dextran or cellulose, or a polyamino acid such as gelatin) or a derivative thereof.

A method for introducing a functional group into a polymer that is used in the present invention is also not particularly restricted. A polymer may also be produced by performing a copolymerization reaction between a monomer having a reactive functional group and a monomer having an anionic group. Furthermore, a polymer may be previously produced and then the above reactive functional group and the anionic group may also be introduced by a so-called polymer reaction. Furthermore, a method that involves performing a copolymerization reaction using a monomer compound having precursors of a reactive functional group and anionic groups and then generating the reactive functional group by an appropriate method is also effective. A polymer that is used in the present invention may also be produced by copolymerization of other (different) monomer components, in addition to a monomer component having a reactive functional group and a monomer component having an anionic groups.

Examples of a monomer having an anionic group, which is used in the present invention, include vinyl sulfonic acid, methallylsulfonic acid, 2-acrylamide-2-methylpropane sulfonic acid, sulfoethyl methacrylate, styrenesulfonic acid, and 2-(phosphonoethyloxy)ethyl methacrylate.

As a monomer having reactive functional groups, which is used in the present invention, a compound disclosed in JP Patent Application No. 2005-46977 can be preferably used. Specifically, typical examples are M1 to M26 shown herein above.

Examples of a monomer having a carboxyl group that is a precursor of carboxylic active ester, which is used in the present invention, include acrylic acid, methacrylic acid, and 4-vinylbenzoic acid.

Examples of another such monomer component that is used in the present invention other than a monomer component having a reactive functional group and a monomer component having an anionic group include the following monomers.

acrylic esters, methacrylic acid esters, and amides of ethylene unsaturated carboxylic acid (e.g., acrylamide, methacrylamide, N-acryloyl morpholine, and N,N-dimethylacrylamide, 2-acrylamide-2-methylpropane sulfonic acid (or a salt thereof));

aromatic monomers (e.g., styrene, vinyltoluene, p-t-butylstyrene, and vinylnaphthalene); other vinyl monomers (e.g., ethylene, propylene, vinyl chloride, vinylidene chloride, triphloroethylene, triphlorochloroethylene, vinyl acetate, vinyl propionate, vinyl alcohol, N-vinyl pyrrolidone, N-vinyl acetoamide, acrylonitrile, and methacrylonitrile);

monomers having an nonionic group (e.g., 2-hydroxyethylacrylate, 2-hydroxyethyl methacrylate, hydroxypropylacrylate, hydroxypropylmethacrylate, 2-hydroxy-3-chloropropylacrylate, β-hydroxyethyl-β'-acryloyloxyethylphthalate, 1,4-butylene glycol monoacrylate, hydroxystyrene, allylalcohol, methallyl alcohol, isopropenyl alcohol, and 1-butenyl alcohol); and monomers having a dipolar ionic group (e.g., [2-(methacryloyloxy)ethyl]dimethyl-(3-sulfopropyl)ammonium hydroxide and [2-(methacryloyloxy)ethyl]phosphorylcholine).

A specific example of a synthetic polymer compound that is used in the present invention is compound 1. Compound 1 is known as a polymeric hardener for silver salt photography. A method for using compound 1 is disclosed in JP Patent Publication (Kokai) No. 2001-264948 A, for example. A surface to which such polymeric hardener has been bound can be preferably used in the present invention. Compound 1 is synthesized by the method disclosed in JP Patent Publication (Kokai) No. 60-61742 A (1985). P-1, P-4, P-6, P-10, P-15, P-16, and P-21 disclosed in JP Patent Publication (Kokai) No. 60-61742 A (1985) can also be preferably used.

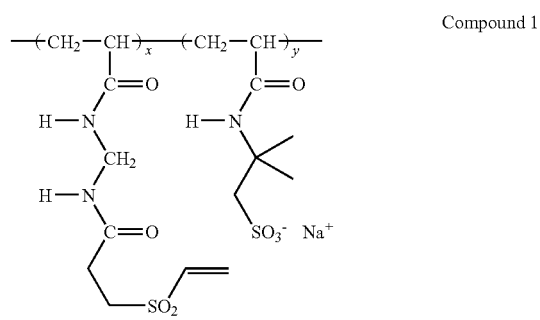

Compound 1

Examples of a natural polymer or a derivative thereof that can be used in the present invention include dextran, cellulose, guar gum, starch, hydroxyethyl dextran, hydroxyethyl cellulose, hydroxyethyl guar gum, hydroxyethyl starch, methyl dextran, methyl cellulose, methyl guar gum, methyl starch, ethyl dextran, ethyl cellulose, ethyl guar gum, ethyl starch, hydroxypropyl dextran, hydroxypropyl cellulose, hydroxypropyl guar gum, hydroxypropyl starch, hydroxyethylmethyl cellulose, hydroxyethylmethyl guar gum, hydroxyethylmethyl starch, hydroxypropylmethyl cellulose, hydroxypropylmethyl guar gum, and hydroxypropylmethyl starch. Of these, dextran, hydroxyethyl dextran, hydroxypropyl dextran, cellulose, hydroxyethyl cellulose, and hydroxypropyl cellulose are preferable. Furthermore, a substituent of such polysaccharide, such as a hydroxyethyl group and a hydroxypropyl group, may have been substituted with a single substituent or with a plurality of substituents. The substitution degree per unit of constitutive monosaccharide residue ranges from 0.1 to 3.0 and particularly preferably ranges from 0.5 to 1.5. Furthermore, the weight average molecular weights of these polysaccharides or the derivatives thereof range from 10,000 to 10,000,000 and particularly preferably range from 100,000 to 1,000,000.

A known method can be used as a method for introducing anionic groups into a natural polymer or a derivative thereof. When sulfonic acid is introduced into polysaccharides, for example, vinyl sulfonic acid, 3-halo-2-hydroxypropanesulfonic acid, 3-halopropanesulfonic acid, 1,3-propane sultone, 1,4-butane sultone, 1,3-butane sultone, or the like is caused to react under alkaline conditions, making it possible to introduce sulfonic acid groups. Polysaccharides are caused to react with chlorsulfonic acid in pyridine, making it possible to introduce sulfuric ester. Polysaccharides are caused to react with phosphorus oxychloride in pyridine, making it possible to introduce phosphoric ester. As a natural polymer having an anionic group, a commercial compound can also be used. Examples of such compound include DS-S18, DS-S5, DS-500, and the like (produced by Meito Sangyo. Co., Ltd.) that are dextran sulfuric acids. Polymers that can be used in the present invention can be produced by introducing a reactive group or a precursor thereof (e.g., carboxyl group) into these natural polymers having an anionic group.

Polymers that can be used in the present invention can also be obtained by introducing an anionic group by the above methods into polysaccharides having a carboxyl group, such as carboxymethyl dextran, carboxymethyl cellulose, or alginic acid. As polysaccharides having a carboxyl group, commercial compounds can be used. Specific examples of such compounds include CMD, CMD-L, and CMD-D40 (produced by Meito Sangyo. Co., Ltd.), which are carboxymethyl dextrans, sodium carboxymethyl cellulose (produced by Wako Pure Chemical Industries, Ltd.), and sodium alginate (produced by Wako Pure Chemical Industries, Ltd.). Polymers that can be used in the present invention can be produced by introducing an anionic group into these natural polymers having a carboxyl group. The above reaction can be used as a method for introducing an anionic group. Furthermore, some carboxyl groups may be activated and then allowed to react with 2-aminoethane-1-sulfonic acid (taurine), 2-aminoethyldihydrogenphosphate, 2-aminoethylhydrogensulfate, or the like, making it possible to introduce sulfonic acid, sulfuric ester, and phosphoric ester, respectively. The proportion of such anionic group to carboxyl group can be controlled using the molar ratio of carboxyl group to an activator, the reaction time, and the reaction frequency.

The polysaccharides having a carboxyl group and a sulfuric ester group can also be used as it is in the present invention. Examples of such polysaccharides include chondroitin C sulfuric acid (produced by Wako Pure Chemical Industries, Ltd.) and heparin sodium (produced by Wako Pure Chemical Industries, Ltd.).

A known method can be used as a method for introducing a reactive functional group into a natural polymer or a derivative thereof. For example, when an acetoacetyl group is introduced into polysaccharides, a method that involves adding a diketene gas after dissolution of polysaccharides in a good solvent such as dimethylformamide, a method that involves adding a diketene gas to powders of polysaccharides, a method that involves allowing polysaccharides to react with acetoacetic ester in a solution so as to perform transesterification, and the like are used. Regarding other methods for introducing a reactive functional group, a method disclosed in JP Patent Application No. 2005-46977 can be preferably used.

According to the present invention, a method for immobilizing a physiologically active substance is provided, which comprises allowing a solution containing a physiologically active substance to come into contact with a surface having a reactive groups capable of chemically immobilizing a physiologically active substance and an anionic group having an acid dissociation constant that is lower than that of a carboxyl group as mentioned above. According to the above immobilization method of the present invention, preconcentration effects (whereby a physiologically active substance is concentrated on the surface of a measurement chip due to electrostatic attraction) can be obtained because an anionic group has been introduced on the surface, even when a solution containing a physiologically active substance and having a pH that is lower than the acid dissociation constant (pKa=3.5) of a carboxyl group is allowed to come into contact with the surface.

In the biosensor obtained as mentioned above, a physiologically active substance is covalently bound via the reactive functional group capable of chemically immobilizing a physiologically active substance, so that the physiologically active substance can be immobilized on the metal surface or metal film.

The agent for immobilizing a physiologically active substance according to the present invention is characterized in that it comprises a polymer having, within a molecule, a reactive group capable of chemically immobilizing a physiologically active substance and an cationic group.

The reactive group capable of chemically immobilizing a physiologically active substance is as mentioned herein above.

The cationic group is also as mentioned herein above.

When a protein to be immobilized is in the form of an aqueous solution, the polymer that is used in the present invention is preferably a water-soluble polymer. A polymer that is not dissolved and that swells in water may also be used. Furthermore, when a protein to be immobilized is in the form of an organic solvent solution, a water-insoluble hydrophobic polymer may also be used.

Furthermore, the number average molecular weight of a polymer that is used in the present invention is preferably 3,000 or more, more preferably 10,000 or more, and particularly preferably 30,000 or more.

Specific examples of the polymer than can be used in the present invention include a polyacrylic acid derivative, a polymethacrylic acid derivative, polyethylene (PE), polypropylene (PP), polybutadiene, polymethylpentene, cycloolefin polymer, polystyrene (PS), acrylonitrile/butadiene/styrene copolymer (ABS), styrene/maleic anhydride copolymer/polyvinyl chloride (PVC), polyethylene terephthalate (PET), polyethylene naphthalate (PEN), nylon 6, nylon 66, cellulose acetate (TAC), polycarbonate (PC), modified polyphenylene ether (m-PPE), polyphenylene sulfide (PPS), polyether ketone (PEK), polyether ether ketone (PEEK), polysulfone (PSF), polyether sulfone (PES), polyphenylene sulfide (PPS), and liquid crystal polymer (LCP). Preconcentration and binding of a physiologically active substance with a pH that is the isoelectric point or higher to a two-dimensional surface are also made possible, when a reactive group capable of chemically immobilizing a physiologically active substance and a cationic group are introduced on the surfaces of the above-mentioned polymer.

Examples of a water-soluble polymer include natural polymers such as a dextran derivative, a starch derivative, a cellulose derivative, and gelatin, and synthetic polymers such as polyvinyl alcohol, polyethylene glycol, polyvinyl pyrrolidone, a polyacrylamide derivative, and polymethylvinylether. When a cationic group is introduced at a high rate, the previously described polymers will become water-soluble polymers. In view of application to a biosensor, natural water-soluble polymers are preferable, and a dextran derivative is particularly preferable.

The polymer used in the present invention may be a synthetic polymer or natural polymer or a derivative thereof. Examples thereof are as mentioned herein above.

To synthesize a polymer that is used in the present invention, a monomer having a reactive group capable of chemically immobilizing a physiologically active substance or a precursor of such reactive group is copolymerized with a monomer having a cationic group. Alternatively, a reactive group capable of chemically immobilizing a physiologically active substance and a cationic group may be introduced later into a polymer.

An example of the former method is a method represented by the following formula. This method is an example of using a monomer having a precursor of a reactive group. The monomer ratio represents a weight ratio.

Furthermore, an example of the latter method (where specifically, the method involves introducing a reactive group capable of chemically immobilizing a physiologically active substance and a cationic group later into a polymer) is a method represented by the following formula. Ellipses in the following formula signify dextran, for example.

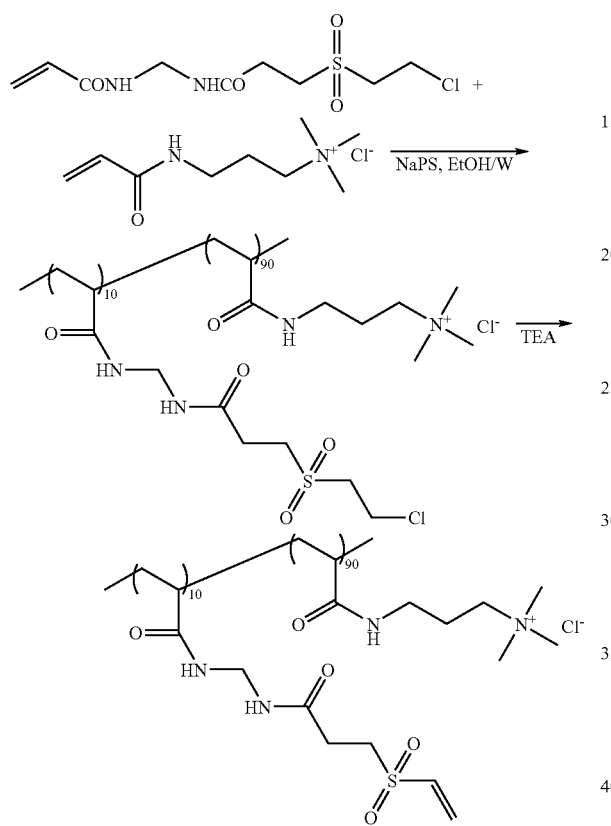

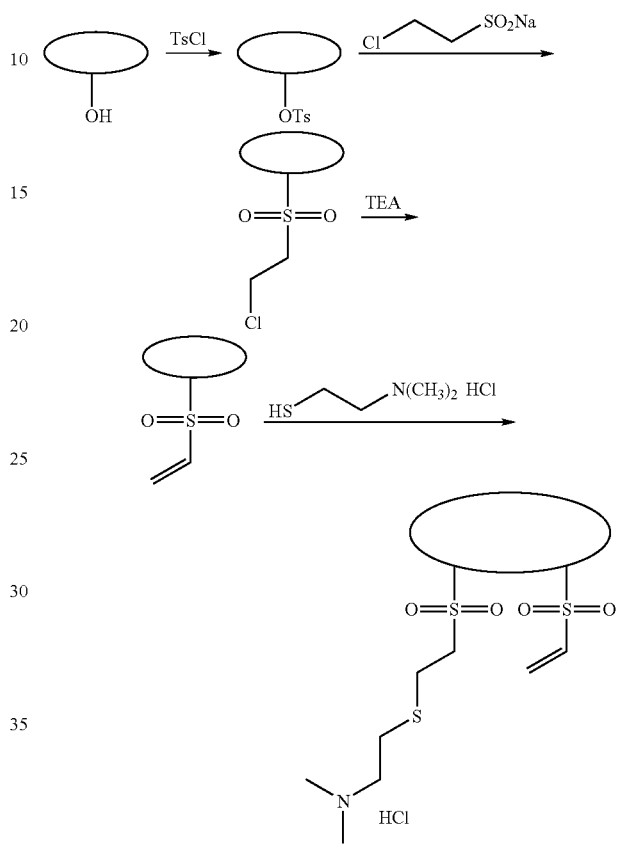

Furthermore, as a comonomer, other polymers can also be used. Any monomers can be used, as long as they can undergo copolymerization. Examples of such monomers include (meth)acrylamides of dimethyl(meth)acrylamide, styrenes, maleic diesters, (meth)acrylic esters, vinyl esters, crotonic esters, itaconic diesters, fumaric diesters, allyl compounds, vinyl ethers, and vinyl ketones. Examples of general monomer compositions (mol) include 1% to 99% of monomer containing a cationic groups and 0.001% to 99% of monomer containing a reactive group, preferably 5% to 70% of monomer containing a cationic group) and 1% to 50% of monomer containing a reactive group, and more preferably 10% to 50% of a monomer containing cationic group and 1% to 30% of monomer containing a reactive group.

A polymerization method may be radical polymerization, anionic polymerization, or cationic polymerization, and is preferably radical solution polymerization or bulk polymerization. A temperature for polymerization is not particularly limited, as long as it enables the relevant reaction to proceed. In view of suppression of coloring and side reactions, such temperature preferably ranges from room temperature to 100° C. Any initiator can be used. The time for polymerization is not particularly limited, as long as it enables conversion to proceed.

The polymer obtained as mentioned above can be used after application to a surface made of organic or inorganic materials. For example, such polymer may be chemically bound to a glass surface via a silane coupling agent having an amino group or may be chemically bound to a gold surface via amino alkanethiol. Furthermore, the polymer can be applied to a substrate surface by spin coating.

Application examples of the agent for immobilizing a physiologically active substance of the present invention include surface plasmon resonance (SPR) measurement, a Quartz Crystal Microbalance (QCM) measurement technique, use of a diagnostic agent using fine particles such as gold particles, and a protein chip.

For example, surface plasmon resonance (SPR) measurement can be performed using a biosensor coated with the agent for immobilizing a physiologically active substance of the present invention.

A physiologically active substance immobilized on the surface for the biosensor of the present invention is not particularly limited, as long as it interacts with a measurement target. Examples of such a substance may include an immune protein, an enzyme, a microorganism, nucleic acid, a low molecular weight organic compound, a nonimmune protein, an immunoglobulin-binding protein, a sugar-binding protein, a sugar chain recognizing sugar, fatty acid or fatty acid ester, and polypeptide or oligopeptide having a ligand-binding ability.

Examples of an immune protein may include an antibody whose antigen is a measurement target, and a hapten. Examples of such an antibody may include various immunoglobulins such as IgG, IgM, IgA, IgE or IgD. More specifically, when a measurement target is human serum albumin, an anti-human serum albumin antibody can be used as an antibody. When an antigen is an agricultural chemical, pesticide, methicillin-resistant *Staphylococcus aureus*, antibiotic, narcotic drug, cocaine, heroin, crack or the like, there can be used, for example, an anti-atrazine antibody, anti-kanamycin antibody, anti-metamphetamine antibody, or antibodies against 0 antigens 26, 86, 55, 111 and 157 among enteropathogenic *Escherichia coli*.

An enzyme used as a physiologically active substance herein is not particularly limited, as long as it exhibits an activity to a measurement target or substance metabolized from the measurement target. Various enzymes such as oxidoreductase, hydrolase, isomerase, lyase or synthetase can be used. More specifically, when a measurement target is glucose, glucose oxidase is used, and when a measurement target is cholesterol, cholesterol oxidase is used. Moreover, when a measurement target is an agricultural chemical, pesticide, methicillin-resistant *Staphylococcus aureus*, antibiotic, narcotic drug, cocaine, heroin, crack or the like, enzymes such as acetylcholine esterase, catecholamine esterase, noradrenalin esterase or dopamine esterase, which show a specific reaction with a substance metabolized from the above measurement target, can be used.

A microorganism used as a physiologically active substance herein is not particularly limited, and various microorganisms such as *Escherichia coli* can be used.

As nucleic acid, those complementarily hybridizing with nucleic acid as a measurement target can be used. Either DNA (including cDNA) or RNA can be used as nucleic acid. The type of DNA is not particularly limited, and any of native DNA, recombinant DNA produced by gene recombination and chemically synthesized DNA may be used.

As a low molecular weight organic compound, any given compound that can be synthesized by a common method of synthesizing an organic compound can be used.

A nonimmune protein used herein is not particularly limited, and examples of such a nonimmune protein may include avidin (streptoavidin), biotin, and a receptor.

Examples of an immunoglobulin-binding protein used herein may include protein A, protein G, and a rheumatoid factor (RF).

As a sugar-binding protein, for example, lectin is used.

Examples of fatty acid or fatty acid ester may include stearic acid, arachidic acid, behenic acid, ethyl stearate, ethyl arachidate, and ethyl behenate.

When a physiologically active substance is a protein such as an antibody or enzyme or nucleic acid, an amino group, thiol group or the like of the physiologically active substance is covalently bound to a functional group located on a metal surface, so that the physiologically active substance can be immobilized on the metal surface.

A biosensor to which a physiologically active substance is immobilized as described above can be used to detect and/or measure a substance which interacts with the physiologically active substance.

In the present invention, it is preferable to detect and/or measure an interaction between a physiologically active substance immobilized on the surface used for a biosensor and a test substance by a nonelectric chemical method. Examples of a non-electrochemical method may include a surface plasmon resonance (SPR) measurement technique, a quartz crystal microbalance (QCM) measurement technique, and a measurement technique that uses functional surfaces ranging from gold colloid particles to ultra-fine particles.

In a preferred embodiment of the present invention, the biosensor of the present invention can be used as a biosensor for surface plasmon resonance which is characterized in that it comprises a metal film placed on a transparent substrate.

A biosensor for surface plasmon resonance is a biosensor used for a surface plasmon resonance biosensor, meaning a member comprising a portion for transmitting and reflecting light emitted from the sensor and a portion for immobilizing a physiologically active substance. It may be fixed to the main body of the sensor or may be detachable.

The surface plasmon resonance phenomenon occurs due to the fact that the intensity of monochromatic light reflected from the border between an optically transparent substance such as glass and a metal thin film layer depends on the refractive index of a sample located on the outgoing side of the metal. Accordingly, the sample can be analyzed by measuring the intensity of reflected monochromatic light.

A device using a system known as the Kretschmann configuration is an example of a surface plasmon measurement device for analyzing the properties of a substance to be measured using a phenomenon whereby a surface plasmon is excited with a lightwave (for example, Japanese Patent Laid-Open No. 6-167443). The surface plasmon measurement device using the above system basically comprises a dielectric block formed in a prism state, a metal film that is formed on a face of the dielectric block and comes into contact with a measured substance such as a sample solution, a light source for generating a light beam, an optical system for allowing the above light beam to enter the dielectric block at various angles so that total reflection conditions can be obtained at the interface between the dielectric block and the metal film, and a light-detecting means for detecting the state of surface plasmon resonance, that is, the state of attenuated total reflection, by measuring the intensity of the light beam totally reflected at the above interface.

In order to achieve various incident angles as described above, a relatively thin light beam may be caused to enter the above interface while changing an incident angle. Otherwise, a relatively thick light beam may be caused to enter the above interface in a state of convergent light or divergent light, so that the light beam contains components that have entered therein at various angles. In the former case, the light beam whose reflection angle changes depending on the change of the incident angle of the entered light beam can be detected with a small photodetector moving in synchronization with the change of the above reflection angle, or it can also be detected with an area sensor extending along the direction in which the reflection angle is changed. In the latter case, the light beam can be detected with an area sensor extending to a direction capable of receiving all the light beams reflected at various reflection angles.

With regard to a surface plasmon measurement device with the above structure, if a light beam is allowed to enter the metal film at a specific incident angle greater than or equal to a total reflection angle, then an evanescent wave having an electric distribution appears in a measured substance that is in contact with the metal film, and a surface plasmon is excited by this evanescent wave at the interface between the metal film and the measured substance. When the wave vector of the evanescent light is the same as that of a surface plasmon and thus their wave numbers match, they are in a resonance state, and light energy transfers to the surface plasmon. Accordingly, the intensity of totally reflected light is sharply decreased at the interface between the dielectric block and the metal film. This decrease in light intensity is generally detected as a dark line by the above light-detecting means. The above resonance takes place only when the incident beam is p-polarized light. Accordingly, it is necessary to set the light beam in advance such that it enters as p-polarized light.

If the wave number of a surface plasmon is determined from an incident angle causing the attenuated total reflection (ATR), that is, an attenuated total reflection angle (θ), the dielectric constant of a measured substance can be determined. As described in Japanese Patent Laid-Open No. 11-326194, a light-detecting means in the form of an array is considered to be used for the above type of surface plasmon measurement device in order to measure the attenuated total reflection angle (θSP) with high precision and in a large dynamic range. This light-detecting means comprises multiple photo acceptance units that are arranged in a certain direction, that is, a direction in which different photo acceptance units receive the components of light beams that are totally reflected at various reflection angles at the above interface.

In the above case, there is established a differentiating means for differentiating a photodetection signal outputted from each photo acceptance unit in the above array-form light-detecting means with regard to the direction in which the photo acceptance unit is arranged. An attenuated total reflection angle (θSP) is then specified based on the derivative value outputted from the differentiating means, so that properties associated with the refractive index of a measured substance are determined in many cases.

In addition, a leaking mode measurement device described in "Bunko Kenkyu (Spectral Studies)" Vol. 47, No. 1 (1998), pp. 21 to 23 and 26 to 27 has also been known as an example of measurement devices similar to the above-described device using attenuated total reflection (ATR). This leaking mode measurement device basically comprises a dielectric block formed in a prism state, a clad layer that is formed on a face of the dielectric block, a light wave guide layer that is formed on the clad layer and comes into contact with a sample solution, a light source for generating a light beam, an optical system for allowing the above light beam to enter the dielectric block at various angles so that total reflection conditions can be obtained at the interface between the dielectric block and the clad layer, and a light-detecting means for detecting the excitation state of waveguide mode, that is, the state of attenuated total reflection, by measuring the intensity of the light beam totally reflected at the above interface.

In the leaking mode measurement device with the above structure, if a light beam is caused to enter the clad layer via the dielectric block at an incident angle greater than or equal to a total reflection angle, only light having a specific wave number that has entered at a specific incident angle is transmitted in a waveguide mode into the light wave guide layer, after the light beam has penetrated the clad layer. Thus, when the waveguide mode is excited, almost all forms of incident light are taken into the light wave guide layer, and thereby the state of attenuated total reflection occurs, in which the intensity of the totally reflected light is sharply decreased at the above interface. Since the wave number of a waveguide light depends on the refractive index of a measured substance placed on the light wave guide layer, the refractive index of the measurement substance or the properties of the measured substance associated therewith can be analyzed by determining the above specific incident angle causing the attenuated total reflection.

In this leaking mode measurement device also, the above-described array-form light-detecting means can be used to detect the position of a dark line generated in a reflected light due to attenuated total reflection. In addition, the above-described differentiating means can also be applied in combination with the above means.

The above-described surface plasmon measurement device or leaking mode measurement device may be used in random screening to discover a specific substance binding to a desired sensing substance in the field of research for development of new drugs or the like. In this case, a sensing substance is immobilized as the above-described measured substance on the above thin film layer (which is a metal film in the case of a surface plasmon measurement device, and is a clad layer and a light guide wave layer in the case of a leaking mode measurement device), and a sample solution obtained by dissolving various types of test substance in a solvent is added to the sensing substance. Thereafter, the above-described attenuated total reflection angle (θSP) is measured periodically when a certain period of time has elapsed.

If the test substance contained in the sample solution is bound to the sensing substance, the refractive index of the sensing substance is changed by this binding over time. Accordingly, the above attenuated total reflection angle (θSP) is measured periodically after the elapse of a certain time, and it is determined whether or not a change has occurred in the above attenuated total reflection angle (θSP), so that a binding state between the test substance and the sensing substance is measured. Based on the results, it can be determined whether or not the test substance is a specific substance binding to the sensing substance. Examples of such a combination between a specific substance and a sensing substance may include an antigen and an antibody, and an antibody and an antibody. More specifically, a rabbit anti-human IgG antibody is immobilized as a sensing substance on the surface of a thin film layer, and a human IgG antibody is used as a specific substance.

It is to be noted that in order to measure a binding state between a test substance and a sensing substance, it is not always necessary to detect the angle itself of an attenuated total reflection angle (θSP). For example, a sample solution may be added to a sensing substance, and the amount of an attenuated total reflection angle (θSP) changed thereby may be measured, so that the binding state can be measured based on the magnitude by which the angle has changed. When the above-described array-form light-detecting means and differentiating means are applied to a measurement device using attenuated total reflection, the amount by which a derivative value has changed reflects the amount by which the attenuated total reflection angle (θSP) has changed. Accordingly, based on the amount by which the derivative value has changed, a binding state between a sensing substance and a test substance can be measured (Japanese Patent Application No. 2000-398309 filed by the present applicant). In a measuring method and a measurement device using such attenuated total reflection, a sample solution consisting of a solvent and a test substance is added dropwise to a cup- or petri dish-shaped measurement chip wherein a sensing substance is immobilized on a thin film layer previously formed at the bottom, and then, the above-described amount by which an attenuated total reflection angle (θSP) has changed is measured.

Moreover, Japanese Patent Laid-Open No. 2001-330560 describes a measurement device using attenuated total reflection, which involves successively measuring multiple measurement chips mounted on a turntable or the like, so as to measure many samples in a short time.

When the biosensor of the present invention is used in surface plasmon resonance analysis, it can be applied as a part of various surface plasmon measurement devices described above.

The present invention will be further specifically described in the following examples. However, the examples are not intended to limit the scope of the present invention.

EXAMPLES

Example A1

This example relates to a method for producing a sensor chip using a hydrophilic polymer (polymeric hardener) having a reactive functional group capable of reacting with a hydroxyl group or an amino group of a physiologically active substance.

(1) Preparation of Gold Surface Substrate

A film was produced on a glass substrate (8 mm in length×80 mm in width×0.5 mm in thickness) by sputtering using a parallel plate type 6-inch sputter system (produced by ULVAC Inc., SH-550) to a chromium thickness of 1 nm on the substrate and to a gold thickness of 50 nm on the chromium. This substrate was treated with a Model-208UV-ozone cleaning system (TECHNOVISION INC.) for 30 minutes, thereby preparing a gold surface substrate.

(2) Preparation of Sample 1 (Comparative Example)

Hydrogel was formed on the gold surface through application of the method disclosed in Japanese Patent No. 2815120. The gold surface substrate prepared in (1) was placed in a petri dish (internal diameter of 16 cm). Ethanol/water (80/20) wherein 5.0 mM 11-hydroxyundecanethiol (produced by DOJINDO LABORATORIES) had been dissolved was poured on the surface. The petri dish was incubated in a shaking incubator at 40° C. for 20 minutes. The surface was washed with 5×50 ml of water, 50 ml of ethanol/water (80/20), and then 5×50 ml of water. Furthermore, the resultant was allowed to come into contact with 2.0 ml of an epichlorohydrin solution in 20 ml of 0.4 M sodium hydroxide and 20 ml of diethylene glycol dimethylether. Reaction was caused to proceed in a shaking incubator at 25° C. for 4 hours. The surface was washed with 2×50 ml of ethanol and 5×50 ml of water. 13.5 g of dextran (T500, Pharmacia) was dissolved in 40.5 ml of water, and then 4.5 ml of 1 M sodium hydroxide was added to the solution. The thus obtained solution was poured on the surface treated with epichlorohydrin. Next, incubation was performed in a shaking incubator at 25° C. for 20 hours. The surface was then washed with 15×50 ml of water at 50° C. 3.5 g of bromoacetic acid was dissolved in 27 g of 2 M sodium hydroxide solution. The thus obtained solution was poured on the surface treated with dextran. After 16 hours of incubation in a shaking incubator at 28° C., the resultant was washed with water. The above reaction with a bromoacetic acid solution, 16 hours of incubation at 28° C., and washing with water were repeated one more time, thereby obtaining sample 1.

(3) Preparation of Sample 2

The gold substrate surface prepared in (1) was placed in a petri dish (internal diameter of 16 cm). Ethanol/water (80/20) wherein 4.0 mM 8-hydroxyoctanethiol (produced by DOJINDO LABORATORIES) and 1.0 mM 11-aminoundecanethiol (produced by DOJINDO LABORATORIES) had been dissolved was poured on the surface. The petri dish was incubated in a shaking incubator at 40° C. for 20 minutes. The surface was washed with 5×50 ml of water, with 50 ml of ethanol/water (80/20), and then with 5×50 ml of water. An alkaline solution (pH 10.0 adjusted with NaOH) wherein a 10 weight % polymeric hardener (P-6) had been dissolved was poured on the surface. The petri dish was incubated in a shaking incubator at 60° C. for 16 hours. The surface was washed with 5×50 ml of water, thereby obtaining sample 2.

(4) Preparation of Sample 3

Sample 3 was obtained by performing similar procedures except for using a polymeric hardener (P-10) instead of the polymeric hardener (P-6) used in the preparation of sample 2.

(5) Preparation of Sample 4

1 M glycine aqueous solution (pH 8.5 adjusted with NaOH) was poured on the surface obtained by procedures similar to those employed for sample 2. The petri dish was incubated in a shaking incubator at 60° C. for 16 hours. The surface was washed with 5×50 ml of water, thereby obtaining sample 4.

(6) Preparation of Sample 5

1 M glycine aqueous solution (pH 8.5 adjusted with NaOH) was poured on the surface obtained by procedures similar to those employed for sample 3. The petri dish was incubated in a shaking incubator at 60° C. for 16 hours. The surface was washed with 5×50 ml of water, thereby obtaining sample 5.

(7) Preparation of Sample 6

1 M 5-aminovaleric acid aqueous solution (pH 8.5 adjusted with NaOH) was poured on the surface obtained by procedures similar to those employed for sample 2. The Petri dish was incubated in a shaking incubator at 60° C. for 16 hours. The surface was washed with 5×50 ml of water, thereby obtaining sample 6.

(8) Preparation of Sample 7

1 M 5-aminovaleric acid aqueous solution (pH 8.5 adjusted with NaOH) was poured on the surface obtained by procedures similar to those employed for sample 3. The petri dish was incubated in a shaking incubator at 60° C. for 16 hours. The surface was washed with 5×50 ml of water, thereby obtaining sample 7.

Example A2

This example relates to immobilization of neutral avidin (produced by PIERCE) on the sensor chips obtained in Example A1.

An aqueous solution containing 0.4 M EDC (1-(3-Dimethylaminopropyl)-3 ethylcarbodiimide) and 0.1 M NHS (N-Hydroxysuccinimide) was allowed to come into contact for 30 minutes with the sensor chips 1 and 4 to 7 produced in Example 1. Next, the resultants were washed with an HBS—N buffer (produced by Biacore, pH 7.4). In addition, the HBS—N buffer was composed of 0.01 mol/l HEPES (N-2-Hydroxyethylpiperazine-N'-2-ethanesulfonic Acid) (pH 7.4) and 0.15 mol/l NaCl. Next, the sensor chips 1 to 7 were set in a surface plasmon resonance apparatus according to the present invention. Each sensor chip was set at a position so that the central position to be exposed to a laser beam was placed longitudinally at the center and placed vertically 40 mm away from the end portions. The chips were covered with members made of polypropylene. Thus, cells each having a width (longitudinal direction) of 1 mm, a length (vertical direction) of 7.5 mm, and a depth of 1 mm were prepared. The solution within each cell was substituted with a neutral avidin solution (100 μg/ml, HBS—N buffer). Each resultant was allowed to stand for 30 minutes, followed by substitution with an HBS—N buffer. With the above procedures, N-avidin was immobilized on the sensor chip surface via covalent bonding. The binding amount in the case of NHS esterified sensor chip 1 represented by the amount of change in resonance signal (RU value) between a value measured before addition of neutral avidin and a value measured (after addition) 3 minutes after completion of substitution with the HBS—N buffer, was determined to be a standard binding amount. The binding amounts in the case of sensor chips 2 to 7 represented by the amounts of change (that is, the amounts of neutral avidin bound) in resonance signal (RU values) between values measured before addition of neutral avidin and values measured (after addition) 3 minutes after the completion of substitution with the HBS—N buffer, were evaluated using relative values. Table 2 shows the thus obtained results.

Example A3

This example relates to a measurement of interaction between the sensor chips 1 to 7 (obtained in Example A2) on which neutral avidin had been immobilized and D-biotin (produced by Nacalai Tesque, Inc.).

After measurement in Example A2, the solution within each cell was substituted with an ethanol amine/HCl solution (1 M, pH 8.5). Activated COOH groups that had remained without reacting with neutral avidin were blocked. Next, the solution within each cell was substituted with D-biotin (1 µg/ml, HBS—N buffer). Each resultant was allowed to stand for 10 minutes, followed by substitution with an HBS—N buffer.

The binding amount in the case of sensor chip 1 represented by the amount of change in resonance signal (RU value) between a value measured before addition of D-biotin and a value measured 3 minutes after washing, was determined to be a standard binding amount. The binding amounts in the case of sensor chips 2 to 7 represented by the amounts of change (that is, the amount of D-biotin bound) in resonance signal (RU values) between values measured before addition of D-biotin and values measured 3 minutes after washing, were evaluated using relative values. Table 2 shows the thus-obtained results.

further proved that an effect of increasing the amount of N-avidin bound was higher in the cases (sensor chips 6 and 7) of using 5-aminovaleric acid as amino acid than in cases (sensor chips 4 and 5) of using glycine as amino acid. It was further proved that a greater amount of N-avidin can be immobilized in cases (sensor chips 6 and 7) of using 5-aminovaleric acid as amino acid than in the comparative example 1 (sensor chip 1).

These amounts of D-biotin bound to the sensor chips on which N-avidin had been immobilized were almost proportional to those of N-avidin immobilized. Thus, it was proved that proteins immobilized on the sensor chips obtained according to the present invention retained their ability to bind to low molecular weight compounds.

Synthesis Example 1

Synthesis of Polymer (P-1) Having Vinylsulfone Group and Quaternary Ammonium Group

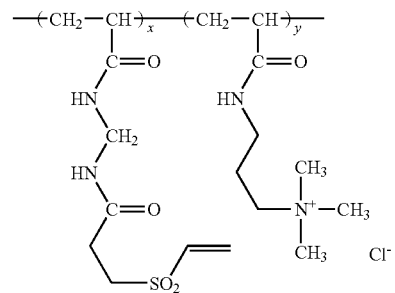

TABLE 2

| Sample No. | Sensor surface | Activation by EDC/NHS | Amount of N-avidin immobilized | Amount of D-biotin bound | Remarks |
|---|---|---|---|---|---|
| 1 | Dextran + bromoacetic acid | Yes | 1.00 | 1.00 | Comparative example |
| 2 | P-6 | No | 0.62 | 0.59 | Present invention |
| 3 | P-10 | No | 0.73 | 0.81 | Present invention |
| 4 | P-6 + glycine | Yes | 0.72 | 0.80 | Present invention |
| 5 | P-10 + glycine | Yes | 0.80 | 0.88 | Present invention |
| 6 | P-6 + 5-aminovaleric acid | Yes | 1.13 | 1.27 | Present invention |
| 7 | P-10 + 5-aminovaleric acid | Yes | 1.21 | 1.33 | Present invention |

It was proved by these examples A1 to A3 that sensor chips 2 and 3 to which N-avidin can be immobilized can be obtained by forming a dense layer on the metal surface using alkanethiol having terminal amino groups and alkanethiol having terminal hydroxyl groups and then causing the amino groups to react with a polymeric hardener. This can be achieved extremely conveniently without using epichlorohydrin or bromoacetic acid, regarding which safety concerns exist. It was proved in sensor chips 4 to 7 that the amount of N-avidin immobilized can be increased by causing reactive functional groups on the sensor chip surface to react with amino acids, followed by activation with EDC/NHS. It was (Monomer Synthesis)

Sodium hydrogen carbonate (65 parts) was added to a solution comprising 350 mL of distilled water and sodium sulfite (56 parts) in a three-neck flask provided with an agitator, a thermometer and a calcium chloride tube, thereby preparing a suspension. 2-chloroethane sulfonylchloride (65 parts) was added dropwise to the suspension at a temperature between 4° C. and 10° C. After dropwise addition, the solution was further agitated at the same temperature for 75 minutes. Subsequently, a 49% sulfuric acid aqueous solution was added dropwise to the reaction solution at a temperature between 4° C. and 10° C. After dropwise addition, reaction was further performed at the same temperature for 1 hour. The thus obtained reaction solution was filtered. Crystals were washed with 100 mL of distilled water. The thus obtained filtrate was then cooled. N,N'-methylenebis acrylamide (62 parts), 370 mL of ethanol, and 120 mL of distilled water were heated at 70° C. and then dissolved almost uniformly, thereby preparing a solution. The solution was added dropwise to the cooled filtrate at a temperature between 5° C. and 10° C. The solution was agitated at the same temperature for 2 hours. The thus obtained reaction solution was allowed to stand in a refrigerator overnight. Viscous solids obtained by filtration were washed with 1.5 L of distilled water and then re-crystallized with 1 L of distilled water/ethanol=1/1. The thus obtained crystals were dried under reduced pressure at 50° C. for 2 hours, thereby obtaining a monomer (42 parts and yield of 37%) having 2-chloroethane sulfone groups.
(Polymerization)

The monomer having 2-chloroethane sulfone groups (1 part), a 75% aqueous solution (4.4 parts) of (3-acrylamide propyl)trimethylammonium chloride, dimethylformamide (25 parts), and dimethyl 2,2'-azobisisobutyrate (0.08 parts) had previously been added to a flask. After 2 minutes of nitrogen purging, the flask was sealed and then polymerization was performed at 65° C. for 3 hours. The temperature of the obtained polymer solution was decreased to 15° C. Triethyl amine (0.36 parts) was added to the solution, followed by 30 minutes of agitation. Subsequently, the polymer was purified using a permeable film and then freeze-dried. The polymer (2 parts) was obtained. FIG. 1 shows the NMR chart of the thus obtained polymer (P-1).

Synthesis Example 2

Synthesis of a Polymer Having a Vinylsulfone Groups and a Tertiary Amino Group Salt (Polymerization)
Polymerization was performed in a manner similar to that of Example 1 except for using a mixture (1:1 (mol)) of N,N'-dimethylaminopropyl acrylamide and p-toluenesulfonic acid instead of (3-acrylamide propyl)trimethylammonium chloride.

Synthesis Example 3

Synthesis of a Polymer Having an Epoxy Groups and a Quaternary Ammonium Group (Polymerization)
Polymerization was performed in a manner similar to that of Example 1 except for using glycidyl methacrylate instead of a monomer having 2-chloroethane sulfone group.

Synthesis Example 4

A polymer that can be used in the present invention was synthesized using GOHSEFIMER Z200H (produced by Nippon Synthetic Chemical Industry Co., Ltd.) that is polyvinyl alcohol wherein an acetoacetyl group capable of reacting with an amino group is introduced.

Deionized water (18.0 g) was added to GOHSEFIMER Z200H (2.0 g) and then the solution was heated to 80° C., thereby obtaining a 10 weight % solution of GOHSEFIMER. 1.0 g of a 1 M N,N-dimethylethylene diamine solution (pH 9.0 adjusted with NaOH) was added to 9.0 g of the solution. The solution was then agitated at room temperature for 24 hours, thereby resulting in successful synthesis of a polymer having an acetoacetyl group and a tertiary amino group. It was confirmed by NMR measurement that approximately 30% of acetoacetyl groups had reacted with N,N-dimethylethylene diamine.

Synthesis Example 5

A polymer having an acetoacetyl group and a quaternary ammonium group was successfully synthesized by performing similar procedures except for using Girard's reagent T (produced by Tokyo Kasei Kogyo Co., Ltd.) instead of the N,N-dimethylethylene diamine used in Synthesis Example 4. It was confirmed that approximately 40% of acetoacetyl group had reacted with Girard's reagent T.

Synthesis Example 6

A polymer having an etoacetyl group and a yridinium group was successfully synthesized by performing similar procedures except for using Girard's reagent P (produced by Tokyo Kasei Kogyo Co., Ltd.) instead of the N,N-dimethylethylene diamine used in Example 4. It was confirmed that approximately 40% of acetoacetyl group had reacted with Girard's reagent P.

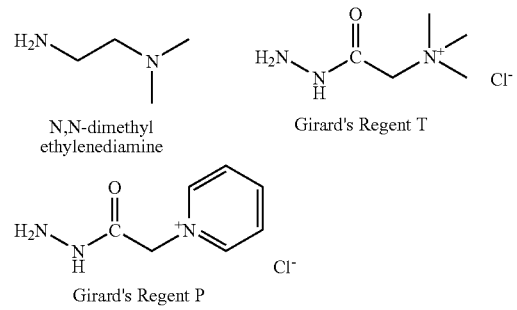

N,N-dimethyl ethylenediamine

Girard's Regent T

Girard's Regent P

Example B1

This example relates to preparation of a sensor chip for immobilizing proteins.
(1) Preparation of Sample 1 (Comparative Example)
A Biacore sensor chip CM-5 (research grade) was used as it is as a surface to which carboxymethyl dextran was bound.
(2) Preparation of Sample 2 (Example)
The experiment was performed using a Biacore sensor chip Au as the surface of a sensor chip, on which gold film alone was formed. The sensor chip Au was subjected to 12 minutes of UV ozone treatment. In an ethanol/water (80/20) mixed solvent containing 4.0 mM 8-hydroxyoctanethiol (produced by DOJINDO LABORATORIES) and 1.0 mM 11-aminoundecanethiol (produced by DOJINDO LABORATORIES) dissolved therein, the sensor chip was allowed to react at 40° C. for 16 hours. The surface was washed with 5×50 ml of water, with 50 ml of ethanol/water (80/20), and then with 5×50 ml of water. Furthermore, the sensor chip was allowed to react at 60° C. for 16 hours in an aqueous solution containing 10 weight % polymer (P-1) dissolved therein. The surface was washed with 5×50 ml of water, thereby obtaining sample 2.

Example B2

This example relates to preconcentration of a protein at a pH that is the isoelectric point or higher on the sensor chip obtained in Example B1. CA (Carbonic Anhydrase produced by SIGMA) was used as a protein. The isoelectric point of CA used herein was approximately pH 5.8 as confirmed through comparison with simultaneously measured markers (Broad pI Kit (pH 3.5-9.3) produced by Amersham Biosciences) in an electrophoresis experiment using AE-8150 (ATTO Corporation). 1 mg of CA was dissolved in 1 ml of an HBS-EP buffer (produced by Biacore, pH7.4). 10 μl of the solution was weighed, and then 90 μl of a carbonate buffer (produced by PIERCE, pH 9.4) was added to the solution, thereby preparing a 0.1 mg/ml CA solution (pH 9.4 and 0.1 mg/ml). The HBS-EP buffer was composed of 0.01 mol/l HEPES (N-2-Hydroxyethylpiperazine-N'-2-ethanesulfonic Acid) (pH 7.4), 0.15 mol/l NaCl, 0.003 mol/l EDTA, and 0.005 mass % surfactant (P20).

Figure 2:
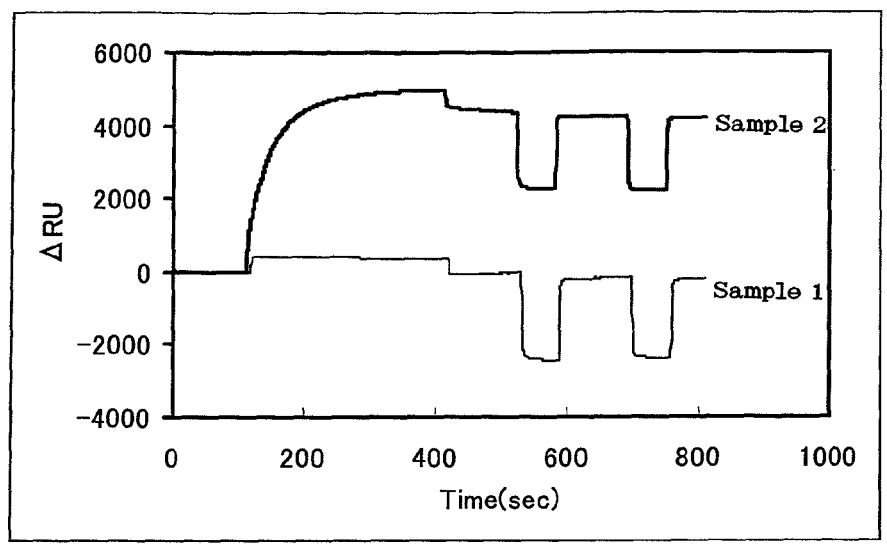
FIG. 2 shows the sensorgram obtained by setting sample 1 and sample 2 of Example B1 in a surface plasmon resonance apparatus and then running a CA (Carbonic Anhydrase) solution.

Sample 1 and the sample 2 prepared in Example B1 were set in a Biacore 3000 (a surface plasmon resonance apparatus produced by Biacore). Preconcentration was examined by running the CA solution (pH 9.4 and 0.1 mg/ml) for 5 minutes and then running 10 mM NaOH twice (1 minute×2). FIG. 2 shows the thus obtained sensorgram.

In the case of sample 1 wherein carboxymethyl dextran had been bound, no preconcentration was observed at pH 9.4, which was higher than the isoelectric point of CA. In contrast, in the case of sample 2 in the present invention, a preconcentration of approximately 4,500 RU was observed. It was thus confirmed that CA corresponding to approximately 4,000 RU remained even after alkaline washing. Specifically, it was proved that preconcentration and immobilization of CA had been achieved at a pH that is the isoelectric point or higher by the surface of the present invention having a reactive group capable of chemically immobilizing a physiologically active substance and a cationic group.

Example B3

Examination similar to that in Example B2 was performed except for using pepsin (produced by Wako Pure Chemical Industries, Ltd.) as a protein. The isoelectric point of pepsin measured was approximately 4.0.

1 mg of pepsin was dissolved in 1 ml of an HBS-EP buffer (produced by Biacore, pH 7.4). 10 μl of the solution was weighed and then 90 μl of an acetate buffer (produced by Biacore, pH 5.0) was added to the solution, thereby preparing a 0.1 mg/ml pepsin solution (pH 5.0 and 0.1 mg/ml).

Figure 3:
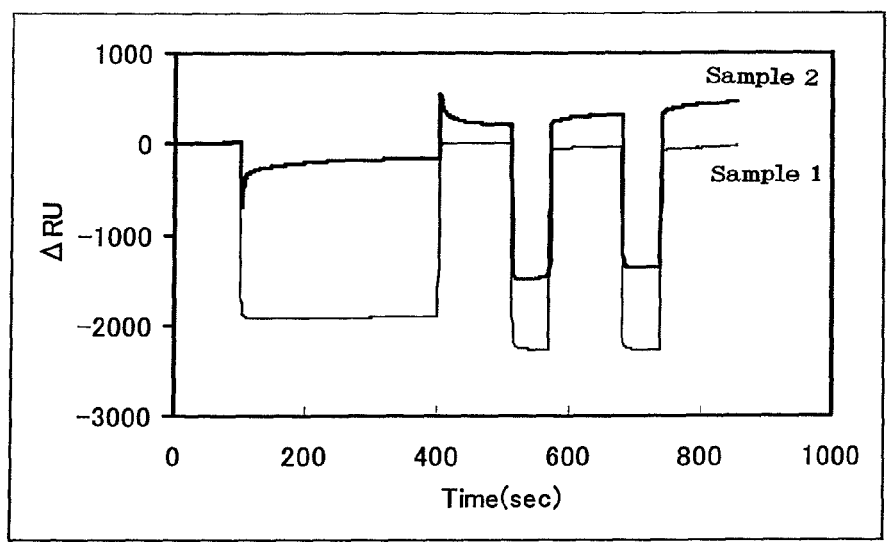
FIG. 3 shows the sensorgram obtained by setting sample 1 and sample 2 of Example B1 in a surface plasmon resonance apparatus and then running a pepsin solution.

Sample 1 and sample 2 prepared in Example B1 were set in a Biacore 3000 (surface plasmon resonance apparatus produced by Biacore). Preconcentration was examined by running the pepsin solution (pH 5.0 and 0.1 mg/ml) for 5 minutes and then running 10 mM NaOH twice (1 minute×2). FIG. 3 shows the thus obtained sensorgram.

In the case of sample 1 wherein carboxymethyl dextran had been bound, no preconcentration was observed at pH 5.0, which was higher than the isoelectric point of pepsin. In contrast, in the case of sample 2 in the present invention, a preconcentration of approximately 1,800 RU was observed. It was thus confirmed that pepsin corresponding to approximately 600 RU remained even after alkaline washing. It was proved that preconcentration and immobilization of an acidic protein such as pepsin are possible with the use of the surface of the present invention.

Example C1

This example relates to the production of a sensor chip for immobilizing proteins.

(1) Preparation of Sample 1 (Comparative Example)

A Biacore sensor chip CM-5 (research grade) was used as it is as a surface to which carboxymethyl dextran was bound.

(2) Preparation of Sample 2 (Example)

As a surface having a carboxyl group and a sulfonic acid group, a surface of Biacore sensor chip CM-5 (research grade), where a part of carboxyl groups was substituted with taurine, was used.

CM-5 was set in a Biacore 3000 (a surface plasmon resonance apparatus produced by Biacore). CM-5 was allowed to come into contact with an aqueous solution containing 0.4 M EDC (1-(3-Dimethylaminopropyl)-3-ethylcarbodiimide produced by DOJINDO LABORATORIES) and 2.8 mM HODhbt (3,4-Dihydro-3-hydroxy-4-oxo-1,2,3-benzotriazine: Tokyo Kasei Kogyo Co., Ltd.) for 5 minutes. CM-5 was further allowed to come into contact with a 1.0 M solution (adjusted at pH 10.0 with NaOH) of taurine (2-aminoethane-1-sulfonic acid: produced by Wako Pure Chemical Industries, Ltd.) for 5 minutes. Thus, a surface where a part of carboxyl groups of carboxymethyl dextran is substituted with sulfonic acid group was prepared. The rate of substitution with sulfonic acid group can be controlled using the activation time with EDC/HODhbt, the reaction time with taurine, and the number of repetitions of such procedures.

Example C2

This example relates to preconcentration and immobilization of a protein at a solution pH that is higher than the pKa value of carboxylic acid and is lower than the isoelectric point (pI) of the protein on 2 types of sensor chip obtained in Example C1.

Neutral avidin (produced by PIERCE) was used as a protein. The isoelectric point (pI) of neutral avidin was approximately pI=6.0 as confirmed through comparison with simultaneously measured markers (Broad pI Kit (pH 3.5-9.3) produced by Amersham Biosciences) in an electrophoresis experiment using AE-8150 (ATTO Corporation).

1 mg of neutral avidin was dissolved in 1 ml of an HBS-EP buffer (produced by Biacore, pH 7.4). 10 μl of the solution was weighed and then 90 μl of an acetate buffer (produced by Biacore, pH 5.0) was added to the solution, thereby preparing a 0.1 mg/ml neutral avidin solution (pH 5.0, 0.1 mg/ml).

Figure 4:
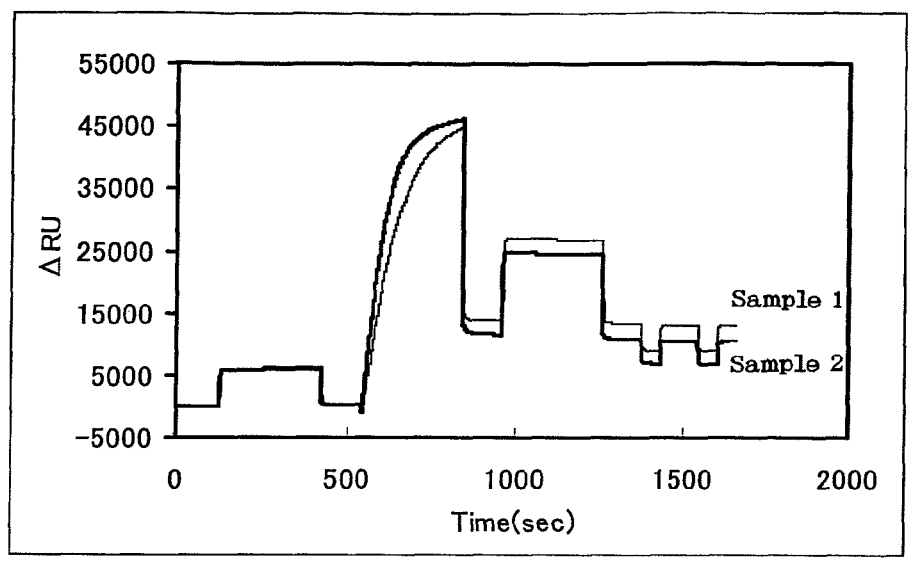
FIG. 4 shows a sensorgram obtained by setting sample 1 and sample 2 of Example C1 in a surface plasmon resonance apparatus and then running a neutral avidin solution having a pH that is higher than the pKa value of carboxylic acid and is lower than the isoelectric point (pI) of neutral avidin.

Sample 1 and sample 2 prepared in Example C1 were set in Biacore 3000 (a surface plasmon resonance apparatus produced by Biacore). Preconcentration and immobilization were examined by running an aqueous solution containing 0.4 M EDC (1-(3-Dimethylaminopropyl)-3-ethylcarbodiimide) and 0.1 M NHS (N-Hydroxysuccinimide), a neutral avidin solution (pH 5.0 and 0.1 mg/ml), and an ethanol amine solution (Biacore), respectively, for 5 minutes and then running 10 mM NaOH twice (1 minute×2). FIG. 4 shows the thus obtained sensorgram.

In the cases of sample 1 wherein carboxyl group alone had been bound and sample 2 wherein a part of carboxyl group had been substituted with sulfonic acid group, the immobilization amounts at pH5.0 (that is higher than the pKa value of carboxylic acid and that is lower than the isoelectric point of neutral avidin) were approximately 13,000 RU and 10,500 RU, respectively. It was proved that almost equivalent preconcentration and immobilization effects can be obtained at this pH.

Example C3

This example relates to preconcentration and immobilization of neutral avidin at a solution pH that is lower than the pKa value of carboxylic acid and is lower than the (pI) of neutral avidin on 2 types of sensor chip obtained in Example C1.

Figure 5:
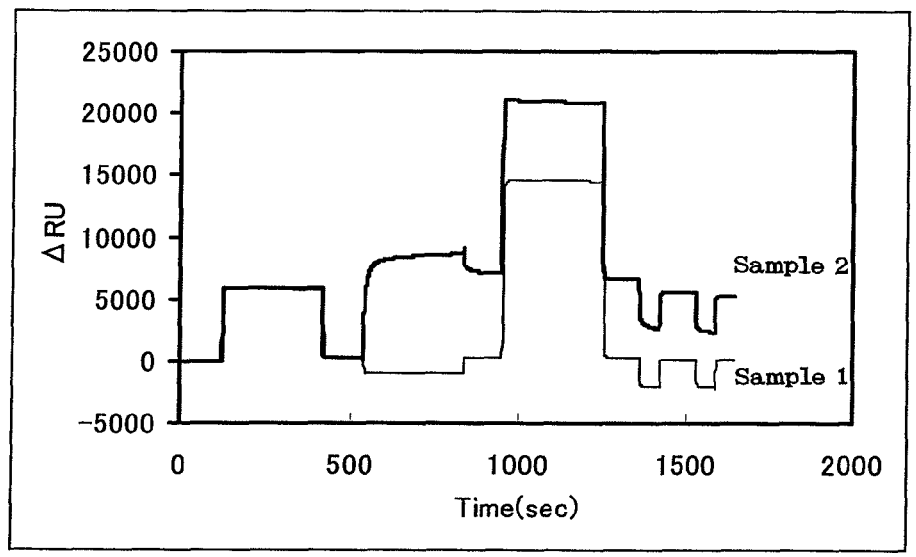
FIG. 5 shows a sensorgram obtained by setting sample 1 and sample 2 of Example C1 in a surface plasmon resonance apparatus and then running a neutral avidin solution having a pH that is lower than the pKa value of carboxylic acid and the isoelectric point (pI) of neutral avidin.

The same procedures were performed as those in Example C2, except for using a glycine buffer (produced by Biacore, pH 1.5) instead of an acetate buffer (produced by Biacore, pH 5.0). FIG. 5 shows the thus obtained sensorgram.

In the case of sample 1 wherein carboxymethyl dextran had been bound, no preconcentration and no immobilization of neutral avidin were observed at pH 1.5 that is the pKa value of a carboxyl group. In contrast, in the case of sample 2 of the present invention, preconcentration of approximately 10,000 RU was observed. It was confirmed that N neutral avidin corresponding to 5,000 RU or more remained after activation, immobilization, binding of ethanol amine, and alkaline washing.

This means that preconcentration and immobilization of neutral avidin had been achieved at a pH that was lower than the pKa value of a carboxyl group by the use of the surface of the present invention having a reactive functional group capable of binding with an amino group via covalent bonding and an anionic group with a pKa value lower than that of carboxylic acid.

Example C4

Example 4 and Example 5 were performed to confirm that similar effects can be obtained even in the cases of proteins other than neutral avidin. In Example C4, CA (Carbonic Anhydrase: produced by SIGMA) was used as a protein. The isoelectric point (pI) of CA was approximately PI=5.8, as confirmed through comparison with simultaneously measured markers (Broad pI Kit (pH 3.5-9.3) produced by Amersham Biosciences) in an electrophoresis experiment using AE-8150 (ATTO Corporation).

Figure 6:
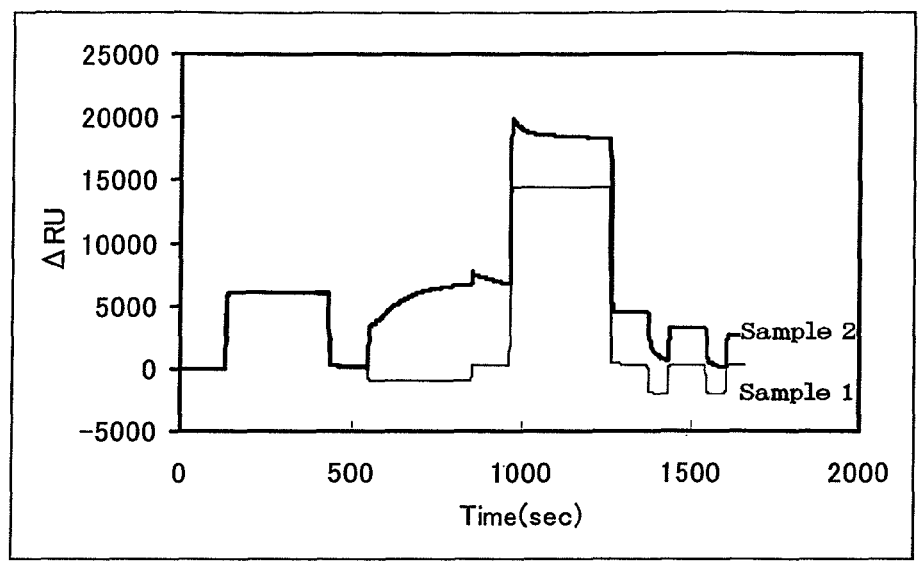
FIG. 6 shows a sensorgram obtained by setting sample 1 and sample 2 of Example C1 in a surface plasmon resonance apparatus and then running a CA solution having a PH that is lower than the pKa value of carboxylic acid and the isoelectric point (pI) of CA (Carbonic Anhydrase).

1 mg of CA was dissolved in 1 ml of an HBS-EP buffer (produced by Biacore, pH 7.4). 10 µl of the solution was weighed and then 90 µl of a glycine buffer (produced by Biacore, pH 1.5) was added to the solution, thereby preparing a 0.1 mg/ml CA solution (pH 1.5, 0.1 mg/ml). In this manner, measurement similar to that in Example C3 was performed. FIG. 6 shows the thus obtained sensorgram.

In the case of sample 1, wherein carboxymethyl dextran had been bound, no preconcentration and no immobilization of the protein were observed at pH 1.5 that is lower than the pKa value of a carboxyl group. In contrast, in the case of sample 2 of the present invention, preconcentration of approximately 6,000 RU was observed. It was confirmed that CA corresponding to approximately 2,500 RU remained after activation, immobilization, ethanol amine reaction, and alkaline washing.

Example C5

In Example C5, fibrinogen (produced by SIGMA) was used as a protein. The isoelectric point (pI) of fibrinogen was approximately pI=5.5 as confirmed through comparison with simultaneously measured markers (Broad pI Kit (pH 3.5-9.3) produced by Amersham Biosciences) in an electrophoresis experiment using AE-8150 (ATTO Corporation).

Figure 7:
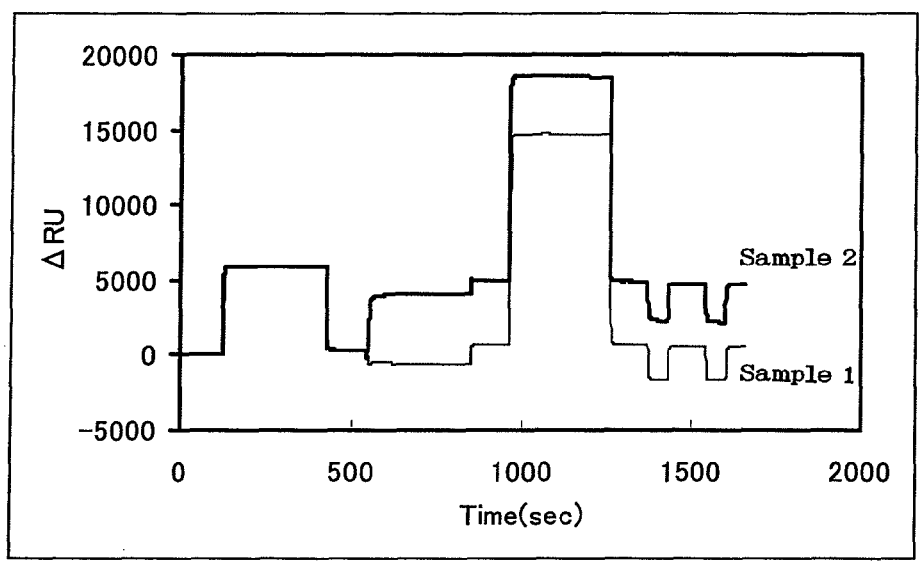
FIG. 7 shows a sensorgram obtained by setting sample 1 and sample 2 of Example C1 in a surface plasmon resonance apparatus and then running a fibrinogen solution at a pH that is lower than the pKa value of carboxylic acid and the isoelectric point (pI) of fibrinogen.

1 mg of fibrinogen was dissolved in 1 ml of an HBS-EP buffer (produced by Biacore, pH 7.4). 10 µl of the solution was weighed and then 90 µl of a glycine buffer (produced by Biacore, pH 1.5) was added to the solution, thereby preparing a 0.1 mg/ml fibrinogen solution (pH 1.5, 0.1 mg/ml). In this manner, measurement similar to that in Example C3 was performed. FIG. 7 shows the thus obtained sensorgram.

In the case of sample 1, wherein carboxymethyl dextran had been bound, no preconcentration and no immobilization of the protein were observed at pH 1.5 that is lower than the pKa value of a carboxyl group. In contrast, in the case of sample 2 of the present invention, preconcentration of approximately 5000 RU was observed. It was confirmed that fibrinogen corresponding to approximately 4,600 RU remained after activation, immobilization, ethanol amine reaction, and alkaline washing.

As shown in Example C2, the surface of the present invention has preconcentration and immobilization abilities equivalent to those of a surface comprising a carboxy group alone at a pH that is the pKa value of carboxylic acid or higher and is the isoelectric point of a protein or lower. Furthermore, it was proved that the surface of the present invention is capable of preconcentrating and immobilizing various proteins even at a pH that is the pKa value of carboxylic acid or lower, although a surface having a carboxy group alone is unable to do the same.

EFFECTS OF THE INVENTION

According to the first embodiment of the biosensor of the present invention, it becomes possible to provide a biosensor and a production method therefor by which hydrogel that enables immobilization of a physiologically active substance can be produced conveniently using safe raw materials.

According to the second embodiment of the biosensor of the present invention, even when a solution containing a physiologically active substance and having a pH that is the isoelectric point of such substance or higher is used, preconcentration effects (whereby a physiologically active substance is concentrated on a measurement chip due to electrostatic attraction) can be obtained, and at the same time the physiologically active substance can be immobilized on the biosensor surface via covalent bonding.

According to the third embodiment of the biosensor of the present invention, even when a solution containing a physiologically active substance and having a pH lower than the acid dissociation constant (pKa=3.5) of a carboxyl group is used, preconcentration effects (whereby a physiologically active substance is concentrated on a measurement chip due to electrostatic attraction) can be obtained, and at the same time the physiologically active substance can be immobilized on the surface of a biosensor via covalent bonding.

Further, by the use of the agent for immobilizing a physiologically active substance of the present invention, a physiologically active substance can be immobilized using charge concentration, even when the pH of a solution of a physiologically active substance such as a protein is the isoelectric point of such substance or higher.

The invention claimed is:

1. A method for immobilizing a physiologically active substance, which comprises allowing a solution containing a physiologically active substance and having a pH that is equal to or higher than an isoelectric point of the physiologically active substance to come into contact with a surface having a reactive group capable of chemically immobilizing the physiologically active substance via a covalent bond and a cationic group, to cause preconcentration and immobilization of the physiologically active substance to the surface, wherein the physiologically active substance is an acidic protein.

2. The method of claim 1 wherein the surface having the reactive group capable of chemically immobilizing the physiologically active substance via a covalent bond and the cationic group is a surface having a water-soluble polymer bound thereto, a surface having a hydrophobic polymer bound thereto, or a surface having a self-assembling monolayer film formed thereon.

3. The method of claim 1 wherein the reactive group capable of chemically immobilizing the physiologically active substance via a covalent bond is a vinylsulfone group or a precursor thereof, a halotriazine group, an epoxy group, a carboxylic active ester group, an aldehyde group, an isooyanate group, or an acetoacetyl group.

4. The method of claim 1 wherein the cationic group is an onium or a precursor thereof.

5. The method of claim 1 wherein the surface having the reactive group capable of chemically immobilizing the physiologically active substance via a covalent bond and the cationic group is formed on a metal.

6. The method of claim 1 wherein the surface having the reactive group capable of chemically immobilizing the physiologically active substance via a covalent bond and the cationic group is a surface of a biosensor.

7. The method of claim 6 wherein the biosensor is a biosensor for surface plasmon resonance analysis.

8. The method of claim 1 wherein the surface has, within a molecule, the reactive group capable of chemically immobilizing the physiologically active substance via a covalent bond and the cationic group.

9. A method for detecting or measuring a substance interacting with a physiologically active substance, which comprises a step of allowing a solution containing a physiologically active substance and having a pH that is equal to or higher than an isoelectric point of the physiologically active substance to come into contact with a biosensor which comprises a surface having a reactive group capable of chemically immobilizing a physiologically active substance via a covalent bond and a cationic group, to cause preconcentration and immobilization of the physiologically active substance to the surface, wherein the physiologically active substance is an acidic protein.

10. The method of claim 9 wherein the surface having the reactive group capable of chemically immobilizing the physiologically active substance via a covalent bond and the cationic group is a surface having a water-soluble polymer bound thereto, a surface having a hydrophobic polymer bound thereto, or a surface having a self-assembling monolayer film formed thereon.

11. The method of claim 9 wherein the reactive group capable of chemically immobilizing the physiologically active substance via a covalent bond is a vinylsulfone group or a precursor thereof, a halotriazine group, an epoxy group, a carboxylic active ester group, an aldehyde group, an isocyanate group, or an acetoacetyl group.

12. The method of claim 9 wherein the cationic group is an onium or a precursor thereof.

13. The method of claim 9 wherein the surface having the reactive group capable of chemically immobilizing the physiologically active substance via a covalent bond and the cationic group is formed on a metal.

14. The method of claim 9 wherein the biosensor is a biosensor for surface plasmon resonance analysis.

15. The method of claim 9 wherein the surface has, within a molecule, the reactive group capable of chemically immobilizing the physiologically active substance via a covalent bond and the cationic group.

* * * * *